(12) United States Patent
Westwood et al.

(10) Patent No.: US 7,868,184 B2
(45) Date of Patent: Jan. 11, 2011

(54) MULTICORE INDAZOLINONE LIBRARY

(75) Inventors: Nicholas James Westwood, Dundee (GB); Nicolas Stanislas Jean Isambert, St Andrews (GB)

(73) Assignee: The University of the University of St. Andrews, Fife (GB)

( * ) Notice: Subject to any disclaimer, the term of this patent is extended or adjusted under 35 U.S.C. 154(b) by 908 days.

(21) Appl. No.: 11/629,150

(22) PCT Filed: Jun. 8, 2005

(86) PCT No.: PCT/GB2005/002230

§ 371 (c)(1),
(2), (4) Date: Dec. 8, 2006

(87) PCT Pub. No.: WO2005/121096

PCT Pub. Date: Dec. 22, 2005

(65) Prior Publication Data

US 2007/0179294 A1 Aug. 2, 2007

(30) Foreign Application Priority Data

Jun. 8, 2004 (GB) ................................ 0412741.1

(51) Int. Cl.
*C07D 231/56* (2006.01)
(52) U.S. Cl. .................................................. 548/361.5
(58) Field of Classification Search ........................ None
See application file for complete search history.

(56) References Cited

U.S. PATENT DOCUMENTS 5,173,496 A * 12/1992 Bruneau et al. ............. 514/338
2007/0129374 A1* 6/2007 Burkamp et al. ............ 514/249

FOREIGN PATENT DOCUMENTS

WO　　WO 03/097610 A　　11/2003　..................231/56
WO　　WO 2004/058720　　*　 7/2004

OTHER PUBLICATIONS

Diaz-Ortiz et al., "Microwave irradiation in solvent-free conditions: an eco-frendly methodology to prepare indazoles, pyrazolopyridines and bipyrazoles by cycloaddition reactions", Green Chemistry, 2(4), 165-172, 2000.*
Molteni, V. et al., "Aqueous one-pot synthesis of pyrazoles, pyrimidines and isoxazoles promoted by microwave irradiation", Chemical Abstracts, 138:187724, 2002.*
Molteni, V. et al., "Recent advances in microwave-assisted synthesis of heterocyclic compounds", Chemical Abstracts, 143:97283, 2005.*
Hayes, B. et al., "Use of microwave irradiation in automated solid phase heterocyclic library synthesis", Chemical Abstracts, 2004:227420, 2004.*
Hayes, B. et al., "Recent Advances in Microwave-Assisted Synthesis", Aldrichimica Acta, 37(2), 66-77, 2004.*
Shaw, A. et al., "Microwave-Assisted Base-Catalyzed Cyclization and Nucleophilic Substitution of O-Azidobenzanilides to Synthesize 1,2-Disubstituted Indazol-3-ones", Synthetic Communications, 39(15), 2647-2663, Jan. 2009, (Abstract).*
Sanjay Menon, et al: "A Parallel Synthesis Demonstration Library of Tri-Substituted Indazoles Containing New Antimutagenic/Antioxidant Hits Related to Benzydamine" *Combinatorial Chemistry and High Throughput Screening*, vol. 6, No. 5, 2003, pp. 471-480.
Franklin Vargas, et al: "Photodegradation of Benzydamine: Phototoxicity of an Isolated Photoproduct on Erythrocytes" *Journal of Pharmaceutical Sciences*, vol. 82, No. 4, Apr. 1993, pp. 371-372.
P. Bruneau, et al: "Indazolinones, a New Series of Redox-Active 5-Lipoxygenase Inhibitors with Built-In Selectivity and Oral Activity" *J. Med. Chem.*, vol. 34, No. 3, 1991, pp. 1028-1036.

* cited by examiner

*Primary Examiner*—Fiona T Powers
(74) *Attorney, Agent, or Firm*—Drinker Biddle & Reath LLP

(57) ABSTRACT

There is provided a method to convert O-functionalized indazolinone-derivatives to the corresponding N2-functionalized indazolinone derivatives, by use of microwave energy or a transition metal catalyst. A preferred catalyst is palladium tetrakis. The method described allows the creation of a library of chemical compounds which can be screened for biological activity.

8 Claims, 19 Drawing Sheets

MULTICORE INDAZOLINONE LIBRARY

The present invention relates to a method of producing a library of indazolinone or indazolone-containing compounds, and to a method for screening the library for therapeutically useful compounds.

Parallel synthesis is a strategy whereby sets of discrete compounds are prepared simultaneously in arrays of physically separate reaction vessels or micro compartments without interchange of intermediates during the assembly process. This strategy allows the creation of a series of individual compounds through reactions performed usually with the aid of automation. This technique is often used to optimise reactions, because of the easy way to change several parameters (concentration, temperature, solvent etc.). The inconvenience of this approach is that a purification step is needed, because the reactions are performed in solution, and the products have to be separated from the reagents, starting material and/or catalyst etc.

In such methods, the quantities created are in general 50 to 100 mg of compound, and the number of created compounds is typically less than 500.

Solid phase combinatorial synthesis is the generation of large collections or libraries of compounds by synthesizing all possible combinations of a set of chemicals on a solid support.

In the laboratory, this approach takes the following form: the solid support is provided in the form of discrete particles, usually made of resin. Initially each discrete particle has multiple copies of the same chemical entity attached. These discrete particles are divided into a number of reaction batches. The batches are each subjected to reaction with different chemical reactants. Pooling of these batches following completion of the reaction results in a pool of discrete particles each particle bearing multiple copies of a single library member type, with many different library member types being represented in the pool. Repetition of the divide, react, and recombine processes results in a library where each discrete particle of solid support carries multiple copies of a single library member type and where the number of different library member types increases with each round of reaction. This approach is also referred to as split and pool synthesis or the "one bead-one compound" approach.

Solid phase combinatorial synthesis thus allows the generation of libraries of compounds wherein;

Excess of reagent can be used to push the reaction to completion.

No purification steps are needed (excess of reagent eliminated by washes) provided the synthetic methodology is highly optimised. The compounds are ready to be screened directly after cleavage from the resin.

Quantities handled: typically less than 15 mg down to low micrograms of each compound is handled.

Yielding a large number of compounds, more than 500 individual compounds.

Large amounts of data about the biological activity of related molecules is generated from screening studies (a large number of independent molecules are tested and so more structure-activity relationship data can be generated).

The chance of hit and lead optimisation is easier.

Combinatorial synthesis pervades many aspects of drug discovery from lead compound identification and target validation, through optimisation to enhancing corporate compound collections.

To make a combinatorial library using solid phase synthesis, it is necessary to:

1. select a core structure; and
2. develop a synthetic route that enables derivatization of the core structure.

In an optimal design, more than one core structure can be easily accessed in order to maximise chemical diversity in a synthetically efficient manner.

Indazolinones (as defined herein) are used as the core structures in the method of the present invention. Indazolinones have a small and rigid chemical skeleton system. Several drugs of interest are an indazolinone-derivative, for example bandazac (a), benzydamine (b), and Seo63 (c) illustrated below or YC-1. Seo63 is prepared via an indazolinone-derivative as an intermediate.

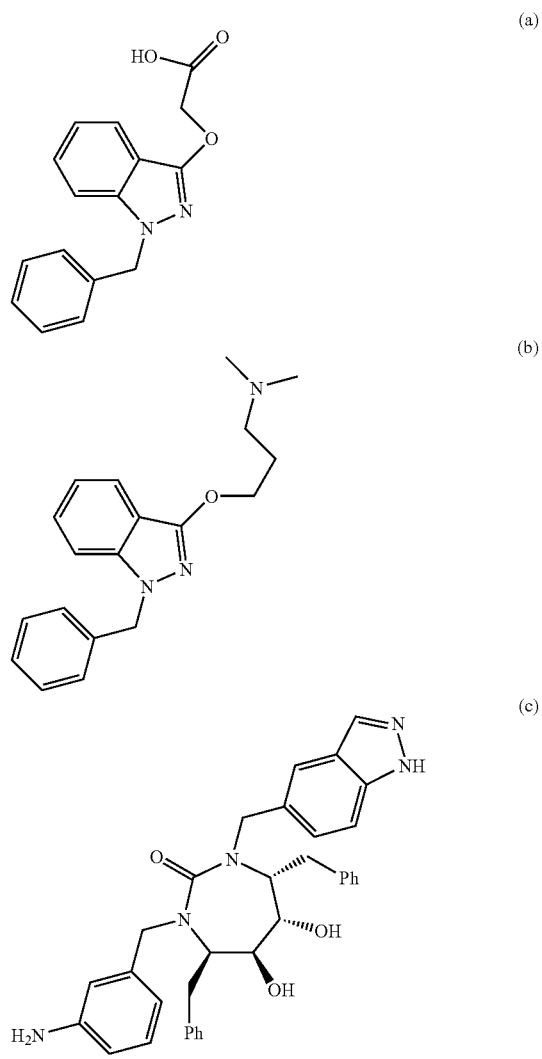

Chemical structures of bandazac (a), benzydamine (b), Seo63 (c).

N1-substituted indazolinones can exist in tautomeric forms (1) and (2). Alkylation of indazolinones on oxygen is used in the synthesis of the indazolone derivative containing anti-inflammatory drugs bandazac (a) and benzydamine (b).

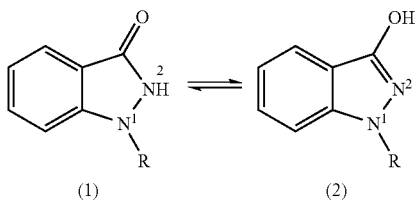

(1)   (2)

ration of the resulting mixture of O— and N2-substituted derivatives. In the context of solid phase combinatorial library generation, however, this situation is unacceptable. In this format, small quantities (nanomoles) of thousands of derivatives are generated and it is unfeasible even using existing automated techniques to purify this number of samples in such small quantities. For library generation it is necessary to develop a sequence of reactions that are very high yielding and selective.

An attempt was made to selectively insert a substituent on one of the two N atoms in an indazolinone ring system (J. Med. Chem. 1991, 34:1492-1503, "Quinazolineacetic Acids and Related Analogues as Aldose Reductase Inhibitors"; Malamas et al.)

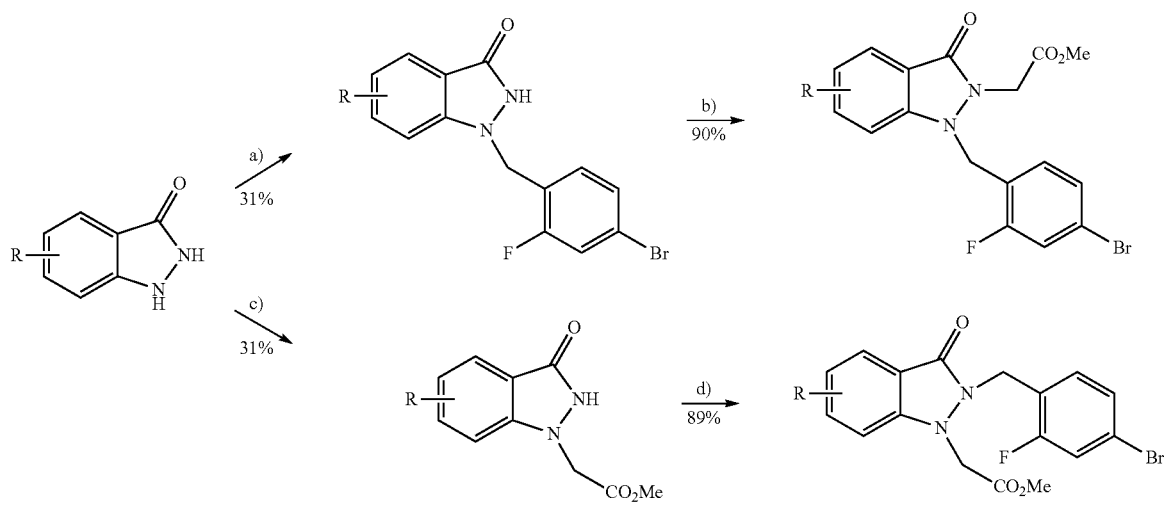

Reaction on the N1 and N2 were made using two kinds of base
a) potassium carbonate, dimethylformamide, 4-bromo-2-fluorobenylbromide, 31%, followed by
b) sodium hydride, dimethylformamide, methylbromoacetate, 90%; or alternatively
c) potassium carbonate, dimethylformamide, methylbromoacetate, 31%, followed by
d) sodium hydride, dimethylformamide, 4-bromo-2-fluorobenylbromide, 89%.

Alkylation on nitrogen instead of oxygen leads to N1, N2-difunctionalised indazolinone-derivatives. Examples of compounds of this type that exhibit biological activity include 5-lipoxygenase inhibition (potential treatment of rheumatoid arthritis, asthma and inflammatory bowel syndrome); in vitro inhibitors of aldose reductase which is a potential target in diabetes therapy and HIV protease inhibitors.

A key synthetic issue in the preparation of indazolinone-derivatives is to achieve selective synthesis of all three possible isomer combinations (ie. O and N1; O and N2; N1 and N2).

The current state of the literature can be summarised as follows. The yields of known processes are low leading to speculation that the reported processes may not be totally selective. In traditional medicinal chemistry, this problem of non-selective functionalisation is usually overcome by sepa- A mixture of N1 and N2 compounds was obtained. The yield of the N1-functionalised compounds was however less than 30%.

A reaction selectively synthesising an N1-functionalised compound has been reported (Synlett, October 1998, pages 1065 to 1066 "An Improved Synthesis of YC-1"; Gordon).

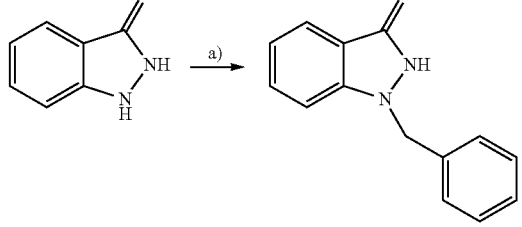

a) benzylchloride, ethanol, sodium hydroxide, 99%.

The reported yield of the N1-functionalised product was 99%. This method does not allow incorporation of a range of substituents in the N1 position. The Applicants repeated this experimental procedure according to the literature, but obtained a mixture of isomers in contradiction to the published results.

The present invention provides a method of converting an O-functionalised indazolinone-derivative into the corresponding N2—functionalised isomer. The method comprises exposing the O-functionalised indazolinone-derivative to microwave energy or a transition metal catalyst.

By the term "indazolinone-derivative" as used herein we refer to a chemical compound having one of the core structures shown below, but including one or more non-hydrogen substituents on the O, N1 Or N2 positions (as available) and/or on the phenyl ring. For the avoidance of doubt, substituted indazolone compounds (see compound 3 below) are included within the term "indazolinone-derivative".

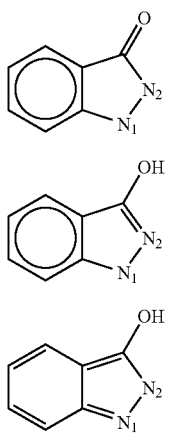

1)

2)

3)

The term "O-functionalised" refers to an indazolinone-derivative of core structure (2) or (3) having a non-hydrogen substituent on the O.

The term "N1-functionalised" refers to an indazolinone-derivative of core structure (1) or (2) having a non-hydrogen substituent on the N1.

The term "N2-functionalised" refers to an indazolinone-derivative of core structure (1) or (3) having a non-hydrogen substitute on the N2.

In one embodiment, the method comprises the following steps;
i) alkylation of an indazolinone-derivative to comprising at least one 0-functionalised indazolinone-derivative having the structure B;
ii) exposing said indozolinone-derivative of step i) to microwave energy or a transition metal catalyst to exclusively form the N2-functionalised indazolinone-derivative having the structure A,

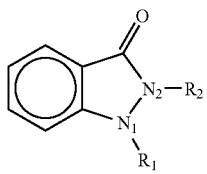
A

-continued

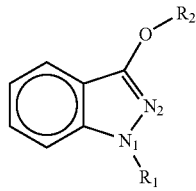
B wherein $R_1$ selected from an alkyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, hydrogen, alkynyl, halogen, cyano, sulfhydryl, carbamoyl, nitro, trifluoromethyl, or heterocyclyl; and
$R_2$ has the following structure:

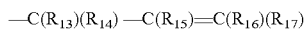

wherein each group $R_{13}$, $R_{14}$, $R_{15}$, $R_{16}$, and $R_{17}$ is independently selected from hydrogen, —$CH_3$ Or —$C_2H_5$, or an aryl group.

In one embodiment $R_2$ has the following structure:

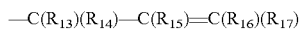

wherein each of $R_{13}$, $R_{14}$, $R_{15}$ and $R_{16}$ is independently selected from hydrogen, —$CH_3$ Or —$C_2H_5$; and $R_{17}$ is an aryl group.

In one embodiment $R_{13}$ to $R_{16}$ are each hydrogen and $R_{17}$ is aryl group.

In one embodiment $R_{17}$ is phenyl.

The reference to any alkyl, aminoalkyl, acylamino, acyloxy, alkoxycarbonyl, alkoxy, alkylaryl, hydroxyalkyl, or thioalkyl group refers to any such group in linear or branched form.

The reference to any alkyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, hydrogen, alkynyl, halogen, cyano, sulfhydryl, carbamoyl, nitro, or trifluoromethyl group, includes any such group in substituted or unsubstituted form, except where specified to the contrary.

In one embodiment the heterocyclyl moiety is substituted with one or more substituents chosen from at least one of alkyl, halo, hydroxy, amino, thio, lower alkoxy, lower alkylthio, lower alkylamino, nitro, phenoxy, benzyloxy, hydrogen or any derivative incorporating phosphorous.

In one embodiment, the reaction mixture contains both N2— and O-functionalised derivatives. Thus, the method comprises the following steps;
i) alkylation of an indazolinone-derivative to form an isomeric mixture comprising at least one N2-functionalised indazolinone-derivative having the structure A and at least one O-functionalised indazolinone-derivative having the structure B;

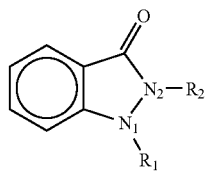
A

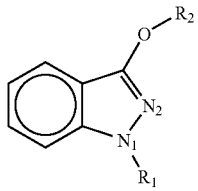

ii) exposing said indozolinone-derivative mixture of step i) to microwave energy or a transition metal catalyst to exclusively form the N2-functionalised indazolinone-derivative (structure A), wherein $R_1$ and $R_2$ are as defined above.

Functional groups present on the N1, N2 Or phenyl ring of the indazolinone core structure can be caused to react through the use of a transition metal catalyst, particularly a palladium catalyst. Consequently the use of transition metal catalysts may not be suitable for the conversion of all O-functionalised indazolinone-derivatives to N2-functionalised indazolinone-derivatives. However microwave energy is suitable for the conversion of O-functionalised indazolinone-derivatives, even in the presence of other substituents.

Preferably when exposed to microwave energy, the O-functionalised indazolinone-derivative is in a polar solvent, suitably dimethyl formamide, dimethyl sulfoxide, alcohols (e.g. ethanol, isopropanol and the like) and water.

Alternatively, the O-functionalised indazolinone-derivative may be in a relatively non-polar solvent, or may not be in a solvent at all (ie the reaction is run neat) when exposed to microwave energy.

When the functional group is present on the N1 ring and is in the form of —NCOX (where X is Ph, OBn, OEt, NHPh etc.) we have occasionally observed a loss of the substituent following exposure to microwave. It is believed that this anomaly is due to the trace presence of water in the reaction mixture.

Suitably the microwave exposure is carried out at a temperature of 150° C. or higher. A pressure of 15 psi or higher can be used.

The indazolinone-derivative may be exposed to microwave radiation for 5 minutes or longer.

In one embodiment the transition metal catalyst is chosen from one or more of catalysts containing palladium, iridium, platinum, mercury, nickel or rhodium. Examples of catalysts include palladium tetrakis, [PdCl$_2$(PhCN)$_2$], Hg(CF$_3$CO$_2$)$_2$, H$_2$[PtCl$_6$], [Pd(PPh$_3$)$_4$], Bis[1,2-bis(diphenylphosphino) ethane]palladium, Bis(tri-t-butylphosphine)palladium, Bis (tricyclohexylphosphine)palladium, trans-DI(μ-acetato)bis [o-(di-o-tolyl-phosphino)benzyl]dipalladium, Diacetatobis (triphenylphosphine)palladium (II), Diaminepalladium(II) nitrite solution, Dichlorobis(acetonitrile)palladium(II), Dichlorobis(benzonitrile)palladium (II), Dichloro(1,2-bis (diphenylphosphino)ethane)palladium(II), Dichloro[1,1'-bis (diphenylphosphino)ferrocene]palladium (II) dichloromethane adduct, trans-Dichlorobis (tricyclohexylphosphine)palladium(II), trans-Dichlorobis (triphenylphospine)palladium(II), trans-Dichlorobis(tri-o-tolylphosphine)palladium (II), Dichloro(1,5-cyclooctadiene) palladium (II), trans-Dichlorodiammine palladium (II), Tetrakis(triphenylphosphine)palladium, Tris(dibenzylidenoacetone)dipalladium, and Tris(dibenzylidenoacetone)dipalladium. A preferred catalyst is palladium tetrakis.

In general the O-functionalised indazolinone-derivative forms the $N_2$-functionalised isomer within minimally half an hour of contact with the transition metal catalyst.

According to a further aspect of the present invention there is provided a library comprising indazolinone-derivatives of at least one of the following general formulae:

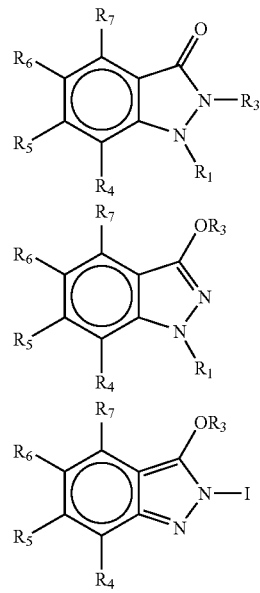

wherein $R_1$ and $R_3$ to $R_7$, are each independently selected from an alkyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, hydrogen, alkynyl, halogen, cyano, sulfhydryl, carbamoyl, nitro, trifluoromethyl, or heterocyclyl group.

The library may also contain other compounds, if required.

In one embodiment compounds in the library are of at least one of the following general formulae:

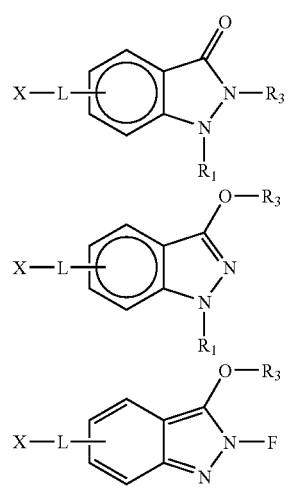

wherein $R_1$ and $R_3$ are as defined above:
L is a linking group; and
X is a solid support.

In one embodiment L represents a group —O—(CH$_2$)$_n$— where n is an integer of 1 to 6 (ie. is 1, 2, 3, 4, 5 Or 6).

In one embodiment X is a resin. Suitable resins include polystyrene resins manufactured to include a suitable chemical linking group, but any chemically inert material having the desired chemical linking groups could alternatively be used. Chemical linking groups useful in this regard include diisopropysilyl or carboxylic acid linkers. Tallarico et al. in J. Comb. Chem., 2001, 3:312 describe the production of a polystyrene resin with diisopropylsilyl linking groups. Suitable resins are also available commercially, for example from Novabiochem (Nottingham, UK).

In one embodiment, compounds in the library are of at least one of the following general formulae:

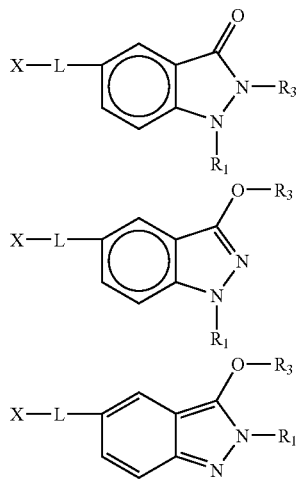

wherein R$_1$, R$_3$ and L and X are as defined above. In one embodiment R$_1$ Or R$_3$ is —CH$_2$Ph. In one embodiment R$_1$ Or R$_3$ is a group R$_2$ as defined above which may optionally be substituted.

According to a further aspect of the present invention there is provided a method of constructing a library of isolated compounds comprising the steps of;

1) exposing an O-functionalised indazolinone to microwave energy or a transition metal catalyst to exclusively form N2-functionalised indazolinone; and
2) diversifying said N2-functionalised indazolinone at selected reactive moieties to generate a library of compounds.

The N2-functionalised indazolinones may be used themselves as intermediates to prepare compounds of N1 functionality or O functionality.

According to a further aspect of the present invention there is provided the use of the library as described above to screen for compounds having bioactive properties (such as 5-lipoxygenase inhibition, aldose reductase inhibition or HIV protease inhibition).

According to a further aspect of the present invention there is provided the use of the library as described above to screen for compounds with therapeutic activity for medical conditions, in particular for rheumatoid arthritis, asthma, inflammatory bowel syndrome, diabetes or HIV.

The present invention will now be further described, by way of illustration only, with reference to the following non-limiting examples and figures in which:

EXAMPLES

Figure 1:
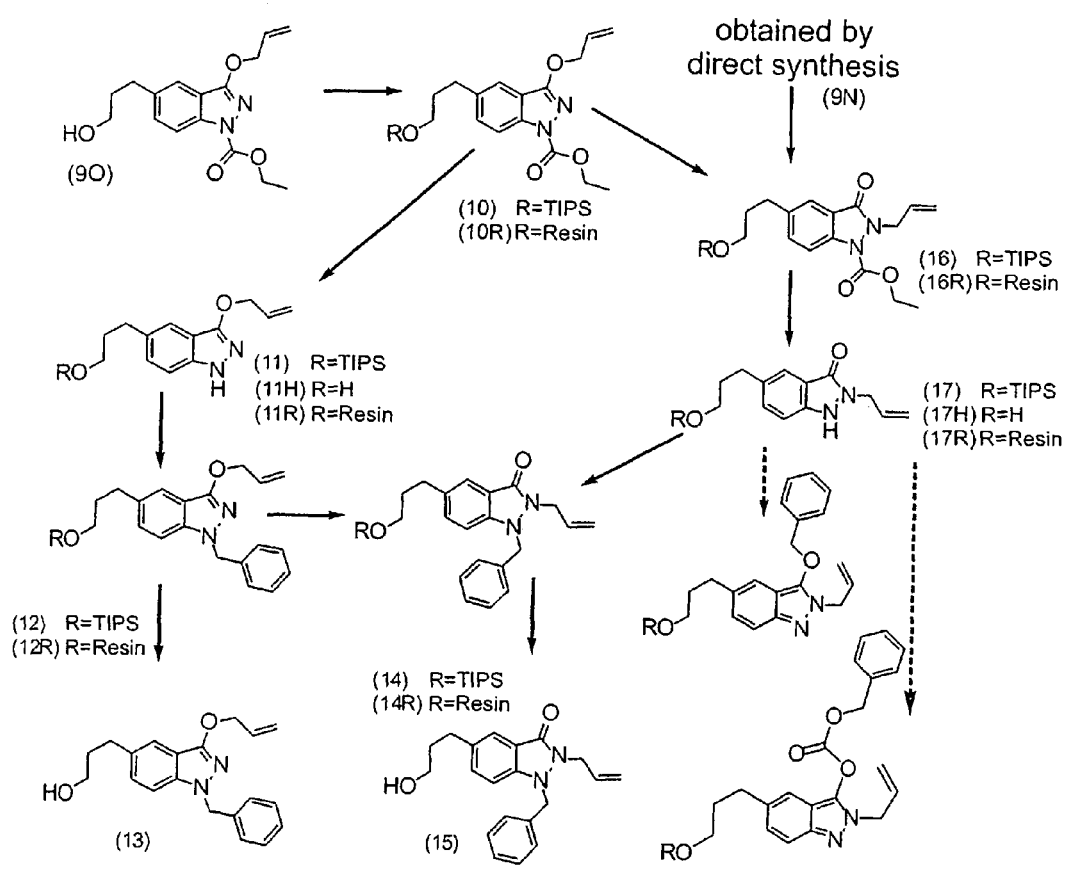
FIG. 1: The reaction pathway for the synthesis of various indazolinone derivatives.

Chemicals and solvents were purchased from Acros, Aldrich, Avocado, Fluka or Lancaster and were used as received unless otherwise stated. Tetrahydrofuran (THF) was dried by refluxing with sodium-benzophenone under N$_2$ atmosphere and collected by distillation. Dichloromethane (CH$_2$Cl$_2$) was dried by heating under reflux over calcium hydride and distilled under N$_2$. Toluene was dried by refluxing over sodium metal under N$_2$ atmosphere. Thin-layer chromatography (TLC) was performed on glass plates coated with Aldrich SIL G-25 UV$_{254}$. Developed plates were air dried and scrutinised under a UV lamp (254/365 nm) and, where necessary, stained with ninhydrin, potassium permanganate or ceric ammomium nitrate to aid identification. Melting points were determined using an Electrothermal 9100 melting point apparatus and are uncorrected. Column chromatography was performed using silica gel Apollo Scientific (40-63 μm). $^1$H Nuclear magnetic resonance (NMR) spectra were recorded on a Bruker Avance 300 (300.1 MHz) or a Varian Gemini 2000 (300 MHz) spectrometer using the deuterated solvent as the lock and the residual solvent as the internal reference in all cases. $^{13}$C NMR spectra using the PENDANT sequence were recorded on a Bruker Avance 300 (75.45 MHz) spectrometer. All other $^{13}$C spectra were recorded on a varion Gemini 2000 (75.45 MHz) spectrometer using composite pulse $^1$H decoupling. $^{19}$F spectra were recorded on a Bruker Avance 300 (282.3 MHz) spectrometer using the deuterated solvent as the lock and the residual solvent as the internal reference. All coupling constants are quoted to the nearest 0.1 Hz. Electron impact mass spectrometry (EIMS) and high-resolution mass spectrometry (HRMS) were carried out on a VG AUTOSPEC mass spectrometer. Chemical ionisation mass spectrometry (CIMS) was carried out on a VG AUTOSPEC instrument.

Example 1

Non-Selective N2— or O-functionalisation

Allylation with NaH, tetrahydrofuran, allyl bromide on N-alloc indazolinone:

Scheme 1:

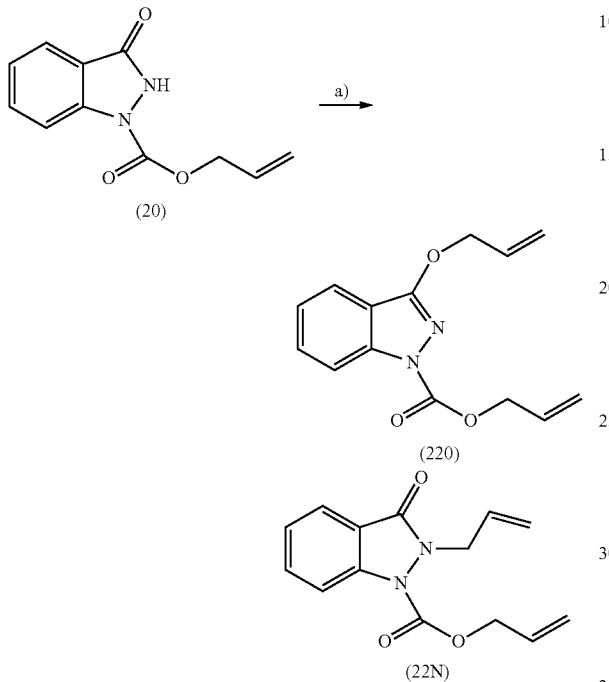

Allylation of N-alloc indazolinone in the presence of sodium hydride.
a) sodium hydride, allyl bromide, tetrahydrofuran.

The solution of (20)(1 g, 4.6 mmol) in dry tetrahydrofuran (10 ml+2×5 ml for washing the flask) was transferred by cannula onto the sodium hydride (0.275 g, 6.8 mmol, 1.5 eq)(previously washed twice with dry hexane), the solution turned to the orange. After three hours stirring under nitrogen, allyl bromide (0.600 ml, 6.88 mmol, 1.5 eq) was added to the orange solution and the solution was stirred overnight at room temperature under nitrogen. The reaction was quenched with ethyl acetate, concentrated in vacuo to remove most of the solvent, and a saturated solution of ammonium chloride was added to the mixture. The solution was extracted with dichloromethane (3×50 ml). The combined organic fractions were dried over magnesium sulphate and concentrated in vacuo. The crude product was purified by flash column chromatography (10% ethyl acetate/hexane) to give (22O)(60 mg, 5%) and (22N)(100 mg, 9%) as a white solids, in a ratio of 1:1.

(22O) m/z (CI) 309(MH$^+$, 100%), 265(10%) 91(10%), $^1$H NMR (300 MHZ, CDCl$_3$) δ 4.81 (2H, dt, J=1.5, 5.5, —CH$_2$—), 4.91 (2H, dt, J=1.5, 5.5, —CH$_2$—), 5.08 (1H, dq, J=1.5, 17.0, =CH$_2$), 5.17 (1H, dq, J=1.5, 10.0, =CH$_2$), 5.30 (1H, dq, J=1.5, 10.5, =CH$_2$), 5.47 (1H, dq, J=1.5, 17.5, =CH$_2$), 5.98 (1H, m, —CH$_2$—), 6.17 (1H, m, —CH$_2$—), 7.05 (1H, td, J=1.0, 7.5, H-6), 7.22 (1H, dt, J=1.0, 8.5, H-5), 7.34 (1H, td, J=1.5, 8.0, H-4), 7.68 (1H, dt, J=1.5, 8.0, H-7), COSY.

(22N) $^1$H NMR (300 MHz, CDCl$_3$) δ 4.30 (2H, d, J=6.5, —CH$_2$—), 4.53 (2H, dt, J=1.0, 6.0, —CH$_2$—), 5.14 (1H, dd, J=1.0, 10.0, =CH$_2$), 5.22 (2H, d, J=27.5, =CH$_2$), 5.25 (1H, dd, J=1.0, 27.5, =CH$_2$), 5.50 (1H, m, —CH=), 5.84 (1H, m, —CH=), 7.18 (2H, t, J=8.0, H-6, H-5), 7.52 (1H, td, J=1.0, 8.5, H-4), 7.86 (1H, d, J=8.0, H-7), COSY.

Example 2

Allylation with Triethylamine, Allyl Bromide in Chloroform:

Scheme 2:

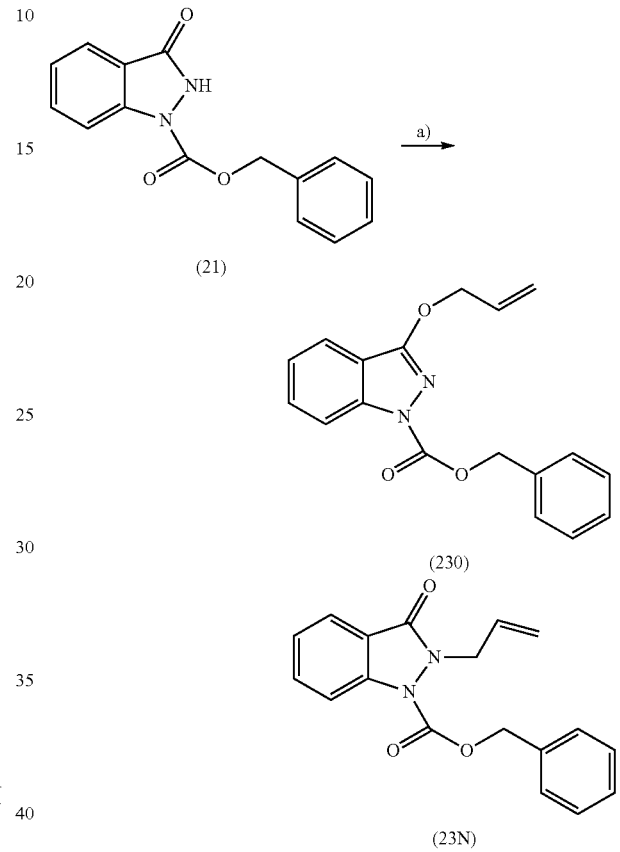

Allylation with allylbromide in chloroform using triethylamine, under reflux.

To a solution of (21)(120 mg, 0.447 mmol) in chloroform (5 ml) was added allyl bromide (155 μL, 3 mmol, 4 eq) and triethylamine (62 μL, 6.72 mmol, 1.5 eq). The solution was stirred under reflux overnight under nitrogen. The reaction solution was cooled at room temperature and quenched with a saturated ammonium chloride solution and extracted with dichloromethane (3×50 ml). The combined organic extracts were dried over magnesium sulphate and concentrated in vacuo. The crude product was purified by chromatography using a gradient starting with 5% of ethyl acetate/hexane to 100% ethyl acetate/hexane to give (23O)(20 mg) and (23N) (60mg).

(23O) $^1$H NMR (300 MHz, CDCl$_3$) δ 4.94 (2H, dt, J=1.0, 6.0, —CH$_2$—), 5.27 (1H, dq, J=1.0, 10.5, =CH$_2$), 5.43 (1H, dq, J=1.0, 17.0, =CH$_2$), 5.44 (2H, s, H-11), 6.08 (1H, m, =CH—), 7.40 (9H, m, ArH).

(23N) $^1$H NMR (300 MHz, CDCl$_3$) δ 4.73 (2H, dt, J=1.5, 7.5, —CH$_2$—), 5.04 (2H, dq$^r$, J=1.5, 8.0, =CH$_2$), 5.33 (2H, s, H-11), 5.60 (1H, m, —CH=), 7.25 (1H, td, J=1.0, 8.0, H-6), 7.36 (5H, m, ArH), 7.53 (1H, td, J=1.5, 7.5, H-5), 7.80 (2H, m, H-4, H-7).

When analogous conditions were used with N1-alloc indazolinone (20) as substrate and benzyl bromide as the alkylating agent; a mixture of (27O) and (27N) was obtained in a ratio 1:4.5 (O:N), yield of 71%.

Scheme 3:

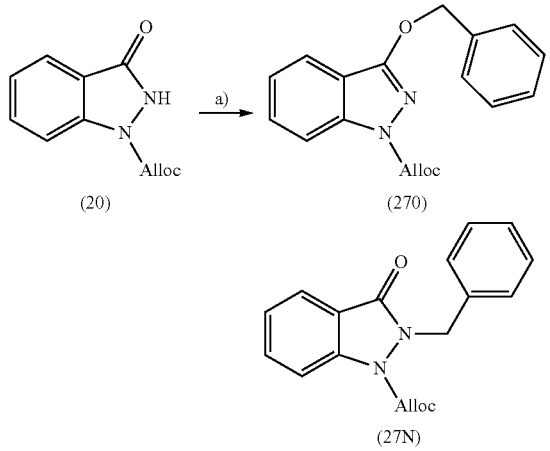

Benzylation of N1-alloc indazolinone.
a) triethylamine, benyl bromide, chloroform uner reflux.

The compound (27N) recrystallised from dichloromethane to give crystals suitable for X-ray analysis. The structure of (27N) was confirmed by this method.

The crude product was purified by flash column chromatography (25% ethyl acetate/hexane) to give the desired product as a light brown powder (1.9 g, 48%), m/z (CI) 268 [MH+100], 91[6], 57[22]n, $^1$H NMR (300 MHz, CDCl$_3$) δ 5.51 (2H, s, H-11), 7.33 (1H, t, J=8.0, ArH), 7.39 (3H, d, J=8.0, ArH), 7.55 (3H, d, J=8.0, ArH), 7.77 (1H, d, J=8.0, H-4), 8.10 (1H, br s, H-7).

Example 3

Synthesis of N1-benzyloxycarbonyl O-cinnamyl indazolinone (21A), and N1 benzyloxycarbonyl N2-cinnamyl indazolinone (21B)

To a solution of (21)(180 mg, 0.7 mmol) in chloroform (10 mL) was added cinnamyl bromide (415 µL, 4 eq.) and triethylamine (100 µL, 1.5 eq.). The solution was stirred under reflux overnight under nitrogen. The reaction was cooled at room temperature and quenched with a saturated ammonium chloride solution and extracted with dichloromethane (3×50 mL). The combined organic extracts were dried over magnesium sulfate and concentrated in vacuo. The crude product was purified by flash column chromatography using a gradient (petroleum ether to 50% petroleum ether/ethyl acetate) to give (21A)(30 mg, 12%) and (21B)(50 mg, 20%).

(21A) $^1$H NMR (300 MHz, CDCl$_3$) δ 5.17 (2H, dd, J=1.00, 6.00 H-19), 5.53 (1H, dt, J=6.00, 16.00, H-20), 6.82 (1H, d, J=16.00, H-21), 7.38 (9H, m, ArH), 7.53 (2H, dd, J=1.00, 7.00, H-5, H-6), 7.71 ((1H, dt, J=1.00, 8.00, H-7), 8.08 (1H, br s, H-7).

(21B) $^1$H NMR (300 MHz, CDCl$_3$) δ 5.00 (2H, dd, J=1.00, 7.00, H-19), 6.05 (1H, dt, J=7.00, 1600, H-20), 6.50 (1H, d, J=16.00, H-21), 7.35 (11H, m, ArH), 7.62 (1H, td, J=1.00, 7.00, H-5), 7.90 (2H, dd, J=1.00, 12.00, H-4, H-6)

Example 4

Rearrangement: from (21A) to (21B) Using Palladium Catalyst (tetrakis triphenylphosphine palladium (0))

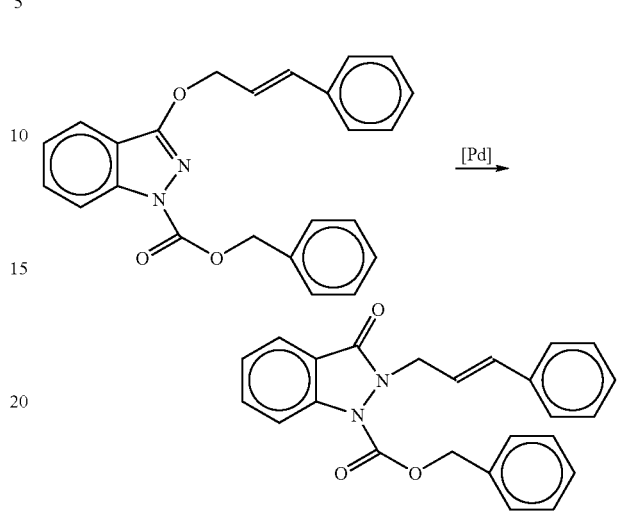

To a solution of (21A), pure (9 mg, 0.02 mmol), dissolved in benzene (2 mL), was added some catalyst with a spatula. The mixture was stirred under argon overnight. The reaction was dried I and purified straight by flash column chromatography using 15% ethyl acetate/hexane to give (21B), in a low yield; the reaction is being improved to access to a quantitative transformation.

(21B) $^1$H NMR (300 MHz, CDCl$_3$) δ 5.00 (2H, dd, J=1.00, 7.00, H-19), 6.05 (1H, dt, J=7.00, 16.00, H-20), 20), 6.50 (1H, d, J=16.00, H-21), 7.35 (11H, m, ArH), 7.62 (1H, td, J=1.00, 7.00, H-5), 7.90 (2H, dd, J=1.00, 12.00, H-4, H-6).

Example 5

Microwave Technique:

Substrate 20 O (Example 1) was dissolved in dimethyl formamide. The rearrangement to 22N was observed at 190° C. under 40 psi after 5 minutes. A rearrangement was not observed when the reaction was carried out at 162° C. under a pressure of 20 psi. The reaction went to completion when temperature and time were increased however (212° C., 60 psi, 10 minutes).

A doping experiment was carried out in order to compare the product obtained by direct synthesis (allylation with sodium hydride) and the product (a) obtained from the microwave-induced rearrangement (b). No new peaks appeared, a part from the TMS peak used as a external signal to prove the addition of b) to c) has occurred. The conclusion of the $^1$H NMR experiment is that the rearrangement carried out using microwave irradiation in dimethylformamide occurred in quantitative yield.

Example 6

Pd Rearrangement

The N1-benzyloxy carbonyl-O-allyl indazolinone (23O) was reacted with a catalytic amount of palladium tetrakis in d6-benzene and $^1$H NMR analysis (300 MHz) of the reaction showed that it went to completion after less than half an hour. The product of this reaction and the product obtained after the allylation (N1-species)(23N) were compared, the two molecules are the same by $^1$H NMR, TLC. The rearrangement occurred quantitatively.

Example 7

Synthesis of N1-ethyloxycarbonyl-N2-allyl-5-(3-hydroxypropyl)indazolinone (9N) and N1-ethyloxycarbonyl-O-allyl-5-(3-hydroxypropyl)indazolinone (9O)

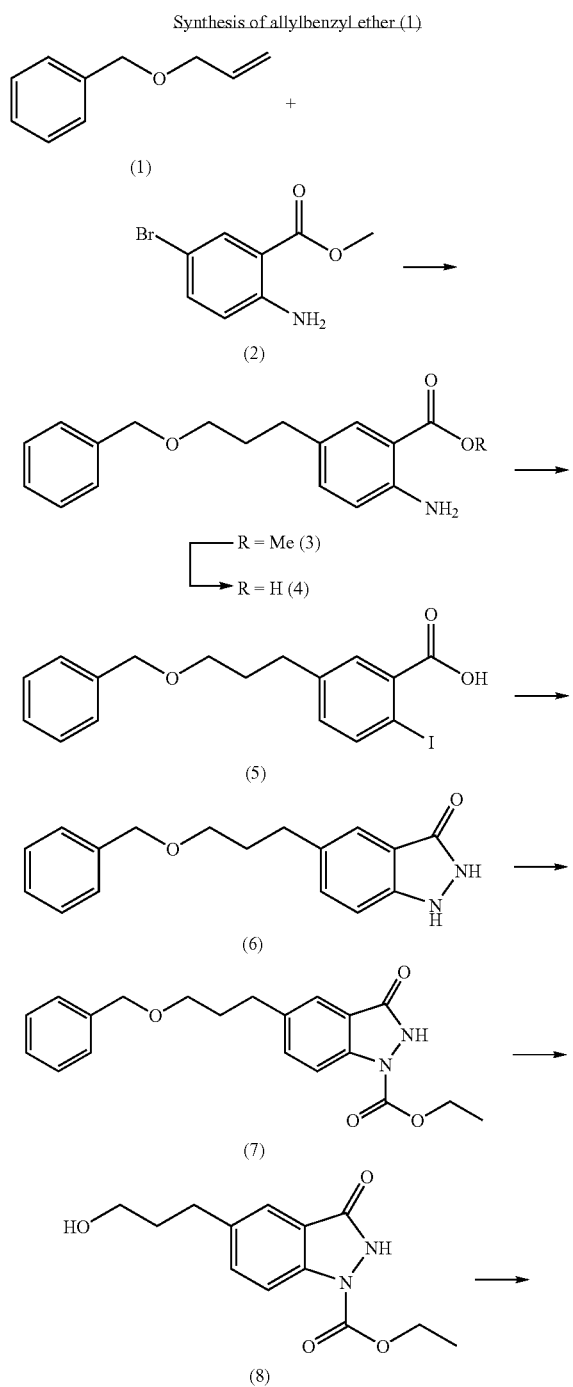

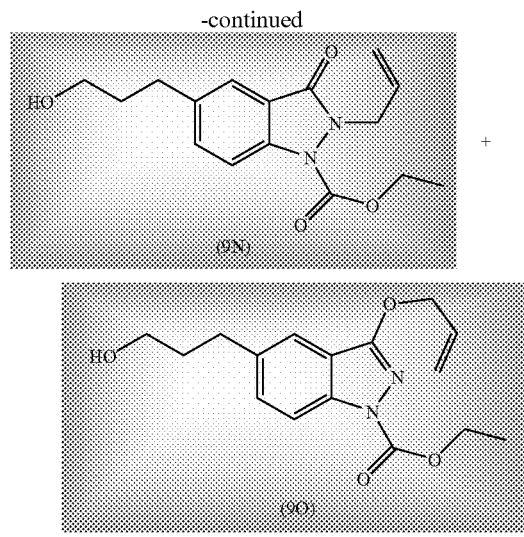

(See Andrew et al., Tetrahedron, 1997, 53:13063). To a suspension of sodium hydride (10.2 g, 254 mmol, 1.1 eq.) in dry THF (250 mL) was added via cannula a solution of benzyl alcohol (25.0 g, 231 mmol, 1.0 eq.) in dry THF (50 mL). The reaction was stirred at room temperature for two hours under an inert atmosphere. Allyl bromide (23.0 mL, 254 mmol, 1.1 eq.) was then added dropwise. The resulting suspension was stirred overnight at room temperature. The solvent was partially removed in vacuo and saturated ammonium chloride solution (100 mL) was added. The aqueous phase was extracted with ethyl acetate (3×150 mL) and the combined organic extracts were dried (MgSO$_4$) and concentrated in vacuo. The crude oil was purified by flash chromatography eluting with 5% ethyl acetate/hexane to give the desired product (1) as a colourless oil (34.0 g, 229 mmol, 99%).

$^1$H NMR δ 7.39-7.27 (m, 5 H; Ar—H), 5.98 (ddt, J=17.3, 10.4, 5.6 Hz, 1 H; C$\underline{H}$=CH$_2$), 5.33 (ddt, J=17.3, 1.6, 1.6 Hz, 1 H: CH=C$\underline{H}_{trans}$), 5.22 (ddt, J=10.4, 1.4, 1.4 Hz, 1 H: CH=C$\underline{H}_{cis}$), 4.54 (s, 2 H; OC$\underline{H}_2$Ph), 4.05 (ddd, J=5.6, 1.4, 1.4 Hz, 2 H; OC$\underline{H}_2$CH).

Synthesis of methyl 2-amino-5-[3-(benzyloxy)propyl]benzoate (3) and 2-amino-5-[3-(benzyloxy)propyl]benzoic acid (4)(One-pot Procedure)

Solid 9-BBN dimer (4.38 g, 35.9 mmol, 1.65 eq.) was transferred to a 500 mL 3-neck flask fitted with a condenser under an inert atmosphere. Freshly distilled dry THF (220 mL) and allylbenzyl ether (1) (5.60 g, 37.8 mmol, 1.74 eq.) were added. The reaction mixture was then stirred for 3 hours at room temperature. The final concentration of the allyl benzyl ether in THF is 0.16M, (see Tallarico et al., J. Comb. Chem., 2001, 3:312) which is the appropriate concentration for the subsequent Suzuki coupling. To the resulting alkylborane-containing THF solution was added methyl 5-iodoanthranilate (2) (5.00 g, 21.7 mmol, 1.0 eq.), tetrakis(triphenylphosphine)palladium(0)(627 mg, 2.50% mol) and NaOH solution (2.0 M, 21.7 mL, 2.0 eq.). The reaction was then refluxed for 24 hours. The presence of 9-BBN by-products made the purification of (3) difficult; for purpose of characterisation, (3) was purified from an aliquot of the reaction by flash chromatography eluting with 20% ethyl acetate/hexane and analysed as follows: $^1$H NMR δ 7.59 (d, J=2.2 Hz, 1 H; Ar—H), 7.26-7.14 (m, 5 H; Ar—H), 6.99 (dd, J=8.4, 2.1 Hz, 1 H; Ar—H), 6.48(d, J=8.4 Hz, 1H: Ar—H), 4.40 (s, 2 H; OCH$_2$Ph), 3.75 (s, 3 H; OCH$_3$), 3.37 (t, J=6.3 Hz, 2 H; OCH$_2$CH$_2$), 2.51 (m, 2 H); ArCH$_2$CH$_2$), 1.79 (m, 2 H; CH$_2$CH$_2$Ar); $^{13}$C NMR δ 168.5, 148.5, 138.5, 134.5, 130.3, 129.5, 128.2, 127.5, 127.4, 116.8, 110.5, 72.8, 69.3, 51.3, 31.3, 31.1; HMQC, HBMC are consistent with the proposed structure (3); LRMS (CI+)m/z: 300 [M+H]$^+$, HRMS (CI+) calculated for C$_{18}$H$_{22}$NO$_3$[M+H]$^+$:300.1600, found: 300.1595.

A solution of aqueous sodium hydroxide (2.0M, 20 mL) was added to the crude reaction mixture and the biphasic solution refluxed for 5 days. The mixture was then cooled, filtered through celite, neutralised with diluted aqueous hydrochloric acid solution to pH 7, and extracted with ethyl acetate (3×100 mL). The combined organic extracts were dried (MgSO$_4$) and concentrated in vacuo. The resulting oil was extracted with hot petroleum ether 40-60 (5×200 mL) and on cooling the desired product (4) was obtained as an off white solid (3.50 g, 12.3 mmol, 60%).

$^1$H NMR δ 7.74 (d, J=2.3 Hz, 1 H), 7.36-7.25 (m, 5 H; Ar—H), 7.16 (dd, J=8.5, 2.3 Hz, 1H; Ar—H), 6.64 (d, J=8.5 Hz, 1 H; Ar—H), 4.51 (s, 2 H; OCH$_2$Ph), 3.48 (t, J=6.4 Hz, 2 H; OCH$_2$CH$_2$) 2.62 (m, 2 H; ArCH$_2$CH$_2$), 1.89 (m, 2 H, ArCH$_2$CH$_2$); $^{13}$C NMR δ 162.6, 144.5, 138.4, 134.5, 132.3, 128.3, 127.6, 127.5, 121.2, 115.8, 111.6, 72.8, 69.3, 31.9, 31.4 HMBC, HMQC are consistent with the proposed structure (4); LRMS (ES$^-$) m/z: 284 [M–H]$^+$; HRMS calculated for C$_{17}$H$_{18}$NO$_3$ [M–H]$^+$: 284.1287, found 284.1279.

Synthesis of 2-iodo-5-[3-(benzyloxy)propyl]benzoic acid (5)

A solution of sodium nitrite (125 mg, 1.77 mmol, 1.03 eq.) in water/acetonitrile (1:1, 5.0 mL) was added with continuous stirring to a solution of (4) (500 mg, 1.75 mmol, 1.0 eq.) in aqueous hydrochloric acid solution (13%, v/v) at such a rate that the reaction temperature remained below 5° C. After addition was complete, the solution was stirred for 15 minutes and potassium iodide (454 mg, 2.74 mmol, 1.56 eq.) in aqueous sulphuric acid solution (10%, v/v, 5 mL) was added. The reaction was then heated for 10 minutes at reflux and cooled to room temperature. Saturated sodium thiosulphate solution (5 mL) was added and the reaction was extracted with ethyl acetate (3×30 mL). The combined organic extracts were dried (MgSO$_4$) and concentrated in vacuo. The crude oil was purified by flash chromatography eluting with 20 to 100% ethyl acetate/hexane to give the desired compound (5) as a viscous oil (593 mg, 1.50 mmol, 85%).

$^1$H δ NMR 7.83 (d, J=7.9 Hz, 1 H; Ar—H), 7.6 (d , J=1.8 Hz, 1 H; Ar—H), 7.28-7.17 (m, 5 H; Ar—H), 6.93 (dd, J=7.9, 1.8 Hz, 1 H; Ar—H), 4.44 (s, 2 H; OCH$_2$Ph), 3.41 (t, J=6.1 Hz, 2 H, OCH$_2$CH$_2$), 2.65 (t, J=7.4 Hz, 2 H; ArCH$_2$CH$_2$), 1.81 (m, 2 H; ArCH$_2$CH$_2$); $^{13}$C NMR δ 170.9, 142.1, 141.6, 138.0, 133.8, 133.2, 132.1, 128.3, 127.7, 127.6, 91.1, 72.8, 68.8, 31.5, 30.7; HMQC and HMBC are consistent with the proposed structure; (IR, MS).

Synthesis of 5-[3-(benzyloxy)propyl]indazolinone (6)

A suspension of (5)(0.80 g, 2.02 mmol, 1.0 eq.), freshly prepared copper powder 115 mg, 1.82 mmol, 0.9 eq.) and 99% hydrazine hydrate solution (440 μL, 14.0 mmol, 7.0 eq.) in isopropanol (12 mL) was refluxed overnight. After cooling, the solution was filtered and solid residues washed with methanol (3×20 mL). The combined organic extracts were then concentrated in vacuo. The crude product was purified by flash chromatography eluting with 50-100% ethyl acetate/hexane to give the desired product (6)(0.270 mg, 0.96 mmol, 52%) as a white solid.

$^1$H NMR δ 9.64 (br s, 1H; NH), 7.45 (s, 1 H; Ar—H), 7.28-7.16 (m, 5 H; Ar—H), 7.12 (dd, J=8.6, 1.5 Hz, 1 H; Ar—H), 6.99 (d, J=8.6 Hz, 1 H; Ar—H), 4.39 (s, 2 H; OCH$_2$Ph), 3.37 (t, J=6.3 Hz, 2 H; OCH$_2$CH$_2$), 2.61 (m, 2 H; ArCH$_2$CH$_2$), 1.85-1.76 (m, 2 H; ArCH$_2$CH$_2$); LRMS (ES$^-$) m/z: 281.1590 [M–H]$^+$; HRMS (ES$^-$): m/z Calculated for C$_{17}$H$_{17}$N$_2$O$_2$ [M–H]$^+$: 281.1290, found 281.1290; $^{13}$C NMR δ 162.6, 144.5, 138.4, 134.5, 132.3, 128.3, 127.6, 127.5, 121.2, 115.8, 111.6, 72.8, 69.3, 31.9, 31.4; HMBC, HSQC are consistent with the proposed structure (6).

Synthesis of N1-ethyloxycarbonyl-5-[3-(benzyloxy) propyl]indazolinone (7)

To a solution of (6)(120 mg, 0.42 mmol, 1.0 eq.) in THF (5 mL) was added triethylamine (0.20 mL, 1.26 mmol, 3.0 eq.). The solution was stirred at room temperature under an inert atmosphere for 30 minutes. To the resulting solution was added ethyl chloroformate (0.13 mL, 1.26 mmol, 3.0 eq.) and the reaction stirred at room temperature for 16 hours. The reaction was then quenched by addition of saturated ammonium chloride solution (20 mL) and extracted with ethyl acetate (3×50 mL). The combined organic extracts were dried (MgSO$_4$) and concentrated in vacuo. The crude material was purified by flash chromatography eluting with 30% ethyl acetate/hexane to give the desired product (7) as an off white solid (150 mg). Morpholine (45 μL, 0.42 mmol, 1.2 eq.) was added to a solution of the white solid (150 mg, 1.0 eq.) in dry THF (15 mL). The reaction was stirred for 30 minutes at room temperature. The reaction was then quenched by addition of saturated ammonium chloride solution (10 mL) and extracted with ethyl acetate (3×30 mL). The combined organic extracts were dried (MgSO$_4$) and concentrated in vacuo. The crude product was purified by recrystallisation in hot ethyl acetate to give (7) as white minute needles (135 mg, 0.38 mmol, 89%).

$^1$H NMR δ 7.95 (br s, 1 H; NH), 7.64 (S, 1 H; Ar—H), 7.44 (dd, J=8.6, 1.6 Hz, 1 H; Ar—H), 7.37-7.27 (m, 5 H; Ar—H), 4.55 (q, J=7.2 Hz, 2 H; OCH$_2$CH$_3$), 4.51 (s, 2 H; OCH$_2$Ph), 3.5 (t, J=6.2 Hz, 2 H; OCH$_2$CH$_2$), 2.85 (m, 2 H; ArCH$_2$CH$_2$), 2.05-1.94 (m, 2 H; ArCH$_2$CH$_2$), 1.53 (t, J=7.2 Hz, 3 H; OCH$_2$CH$_3$); $^{13}$C NMR δ 160.1, 150.1, 138.4, 137.7, 132.2, 128.3, 127.6, 127.5, 120.2, 117.6, 114.2, 72.1, 69.1, 63.6, 32.0, 31.5, 14.3; LRMS (ES$^-$) m/z: 353 [M–H]$^+$; HRMS Calculated for C$_{20}$H$_{21}$N$_2$O$_4$ [M–H]$^+$: 353.1501, found: 353.1489;

Synthesis of N1-ethyloxycarbonyl-5-(3-hydroxypropyl)indazolinone (8)

To a solution of (7)(400 mg, 1.13 mmol, 1.0 eq.) in dry THF (15 mL) in an autoclave was added a catalytic amount of palladium on carbon (10%). The reaction mixture was degassed under vacuum and charged with hydrogen (20 bars). The reaction was stirred at room temperature for five days, filtered through celite and concentrated in vacuo. The solid residues were washed with methanol (3×20 mL), the combined organic extracts were concentrated in vacuo to give the desired product (8) as a white solid (260 mg, 0.99 mmol, 86%).

$^1$H NMR δ 7.81 (d, J=8.4 Hz, 1 H; Ar—H), 7.48 (s, 1 H; Ar—H), 7.37 (d, J=8.4 Hz, 1 H; Ar—H), 4.38 (q, J=7.1 Hz, 2 H; OCH$_2$CH$_3$), 3.50 (t, J=6.3 Hz, 2 H; OCH$_2$CH$_2$), 2.71 (t, J=7.7 Hz, 2 H, ArCH$_2$CH$_2$), 1.83-1.74 (m, 2 H; ArCH$_2$CH$_2$), 1.36 (t, J=7.1 Hz, 3 H; OCH$_2$CH$_3$); $^{13}$C NMR ([d6]DMSO) δ 152.2, 151.7, 141.6, 129.7, 123.7, 111.7, 109.6, 105.8, 55.0, 52.3, 25.8, 23.0, 5.2; LRMS (ES$^+$) m/z: 287 [M+Na]$^+$; HRMS (ES$^+$) Calculated for C$_{13}$H$_{16}$N$_2$O$_4$Na [M+Na]$^+$: 287.1008, found: 287.1011.

Synthesis of N1-ethyloxycarbonyl-N2-allyl-5-(3-hydroxypropyl)indazolinone (9N) and N1-ethyloxycarbonyl-O-allyl-5-(3-hydroxypropyl)indazolinone (9O)

To a solution of (8)(310 mg, 1.17 mmol, 1.0 eq.), allyl alcohol (1.19 mL, 17.6 mmol, 15 eq.), triphenylphosphine (338 mg, 1.29 mmol, 1.05 eq.) in toluene (50 mL) was added slowly diethylazodicarboxylate (0.20 mL, 1.29 mmol, 1.05 eq.) under an inert atmosphere. The reaction was stirred at room temperature for 16 hours. The solvent was partially removed by evaporation, the reaction quenched by addition of saturated ammonium chloride solution (20 mL) and extracted with ethyl acetate (3×25 mL). The combined organic extracts were dried (MgSO$_4$) and concentrated in vacuo. The crude material was purified by flash chromatography eluting with 10%-20% ethyl acetate/hexane to give (9O)(103 mg, 0.35 mmol, 30%) as an off white solid and (9N)(208 mg, 0.70 mmol, 60%) as an off white solid.

(9O): $^1$H NMR δ 7.92 (br s, 1 H; Ar—H), 7.43 (m, 1 H; Ar—H), 7.32 (dd, J=8.7, 1.6 Hz, 1 H; Ar—H), 6.09 (ddt, J=17.2, 10.4, 5.7 Hz, 1 H; NCH$_2$CH), 5.43 (ddt, J=17.2, 1.5, 1.5 Hz, 1 H; CH=CH$_{trans}$), 5.27 (ddt, J=10.4, 1.4, 1.4 Hz, 1 H; CH=CH$_{cis}$), 4.94 (ddd, J=5.7, 1.4, 1.4 Hz, 2 H; NCH$_2$CH), 4.47 (q, J=7.1, 2 H; OCH$_2$CH$_3$), 3.31 (t, J=6.3 Hz, 2 H; OCH$_2$CH$_2$), 2.74 (m, 2H; ArCH$_2$CH$_2$), 1.86 (m, 2 H; ArCH$_2$CH$_2$); 1.42 (t, J=7.1Hz, 3 H; OCH$_2$CH$_3$); (9N): $^1$H NMR δ 7.79 (dd, J=8.5, 0.7 Hz, 1 H; Ar—H), 7.71 (dd, J=1.9, 0.7 Hz, 1 H; Ar—H), 7.48 (dd, J=8.5, 1.9 Hz, 1 H; Ar—H), 5.72 (ddt, J=17.1, 10.1, 6.3 Hz, 1 H; NCH$_2$CH), 5.23 (ddt, J=17.1, 1.4, 1.4 Hz, 1 H; CH=CH$_{trans}$), 5.17 (ddt, J=10.1, 1.3, 1.3 Hz, 1 H; CH=CH$_{cis}$), 4.83 (dt, J=6.3, 1.3 Hz, 2 H; NCH$_2$CH), 4.44 (q, J=7.1 Hz, 2 H; OCH$_2$CH$_3$), 3.68 (t, J=6.3 Hz, 2 H; OCH$_2$CH$_2$), 2.81 (m, 2 H; ArCH$_2$CH$_2$), 1.92 (m, 2 H; ArCH$_2$CH$_2$), 1.45 (t, J=7.1 Hz, 3 H; OCH$_2$CH$_3$).

Example 8

Synthesis of Various Indazolinone Derivatives to Be Part of a Librairie and which Includes the Use of Methods According to the Invention. FIG. 1 Shows the Synthetic Pathways of Indazolinone Derivatives (10) to (15).

Synthesis of N1-ethyloxycarbonyl-O-allyl-5-[3-(triisopropylsilyloxy)propyl]indazolinone (10) on TIPS To a solution of (9O)(40.0 mg, 0.13 mmol, 1.0 eq.) in dry THF (5 mL) was added triethylamine (1.01 mL, 2.60 mmol, 20.0 eq.). Triisopropylsilyltriflate (as a mimic for a solid support resin)(0.52 mL, 1.95 mmol, 15.0 eq.) was added and the reaction mixture stirred for 30 minutes at room temperature. The reaction was quenched by addition of saturated ammonium chloride solution (10 mL) and extracted with ethyl acetate (3×15 mL). The combined organic extracts were dried (MgSO$_4$) and concentrated in vacuo. The crude oil was purified by flash chromatography eluting with hexane to give the desired product (10) as a colourless oil (57 mg, 0.12 mmol, 95%).

$^1$H NMR δ 7.91 (br d, 1H; Ar—H), 7.44 (dd, J=1.6, 0.8 Hz, 1 H; Ar—H), 7.32 (dd, J=8.7, 1.6 Hz, 1 H; Ar—H), 6.08 (ddt, J=17.2, 10.5, 5.8Hz, 1 H; CH=CH$_2$), 5.42 (ddt, J=17.2, 1.5, 1.5 Hz, 1 H; CH=CH$_{trans}$), 5.26 (ddt, J=10.5, 1.5, 1.5 Hz, 1 H; CH=CH$_{cis}$), 4.93 (ddt, J=5.8, 1.5, 1.5 Hz, 2 H, OCH$_2$CH), 4.46 (q, J=7.1 Hz, 2 H; OCH$_2$CH$_3$), 3.63 (t, J=6.1 Hz, 2 H; OCH$_2$CH$_2$), 2.76 (m, 2 H; ArCH$_2$CH$_2$), 1.85-1.76 (m, 2 H, ArCH$_2$CH$_2$), 1.42 (t, J=7.1 Hz, 3 H; OCH$_2$CH$_3$), 0.99 (m, 21 H; Si[CH$_2$(CH$_3$)$_2$]$_3$).

Synthesis of N1-ethyloxycarbonyl-N2-allyl-5-[3-(triisopropyloxy)propyl]indazolinone on Poly-TIPS Resin (10R)

Treatment of the poly-TIPS resin with 2,6-lutidine (8.0 equiv. relative to Si) for 15 minutes followed by addition of 0.5 mL of an azeotropically dried 10.M solution of 9O/9N (2.0 equiv.) resulted in a colorless resin. The beads were then gently agitated for an additional 10 hours under N$_2$ atmosphere. The beads were drained, exposed to atmosphere, and subjected to the following wash protocol: CH$_2$Cl$_2$ (2×3 mL for 45 minutes), THF (2×3 mL for 30 minutes), THF/IPA (3:1, 2×3 mL for 30 minutes), THF/H$_2$O (3:1, 2×3 mL for 30 minutes), THF/IPA (3:1, 2×3 mL for 30 minutes), THF/IPA (3:1, 2×3 mL for 30 minutes), DMF (2×3 mL for 30 minutes), THF (2×3 mL for 30 minutes). The resin was air-dried for 3 h and then placed under hi-vac for 24 h to remove trace of solvent and H$_2$O. The mass of the loaded and dried resin indicated an apparent loading efficiency of 35% based on weight gain.

Synthesis of N1-ethyloxycarbonyl-N2-allyl-5-[3-(triisopropyloxy)propyl]indazolinone on TIPS (16)

To a solution of (9N)(52 mg, 0.17 mmol, 1.0 eq.) in dry THF (5 mL) was added triethylamine (0.12 mL, 0.85 mmol, 5.0 eq.) and triisopropylsilyltriflate (0.09 mL, 0.34 mmol, 2.0 eq.) under an inert atmosphere. The solution was stirred at room temperature for 30 minutes. The reaction mixture was quenched by addition of saturated ammonium chloride solution (15 mL) and extracted with ethyl acetate (3×15 mL). The combined organic extracts were dried (MgSO$_4$) and concentrated in vacuo. The crude material was purified by flash chromatography eluting with 10% ethyl acetate/hexane to give the desired product (16) as a colourless oil (80 mg, 0.17 mmol, 100%).

$^1$H NMR δ 7.71 (d, J=8.5 Hz, 1H; Ar—H), 7.63 (d, J=1.7 Hz, 1H; Ar—H), 7.40 (dd, J=8.5, 1.7 Hz, 1H; Ar—H), 5.65 (ddt, J=16.5, 10.1, 6.2 Hz, 1H; CH=CH$_2$), 5.12 (m, 2H; CH=CH$_2$), 4.76 (m, 2H; NCH$_2$CH), 4.36 (q, J=7.1 Hz, 2H; OCH$_2$CH$_3$), 3.64 (t, J=6.1 Hz, 2H; OCH$_2$CH$_2$), 2.73 (m, 2H; ArCH$_2$CH$_2$), 1.80 (m, 2H; ArCH$_2$CH$_2$), 1.38 (t, J=7.1 Hz, 2H; OCH$_2$CH$_3$), 0.99 (m, 21H; Si[CH$_2$(CH$_3$)$_2$]$_3$); $^{13}$C NMR δ 164.7, 151.0, 141.6, 139.2, 134.4, 131.7, 122.9, 118.9, 118.8, 115.1, 63.8, 62.2, 49.2, 34.6, 31.5, 18.0, 17.7, 12.0.

Alternative Synthesis by Palladium Rearrangement of 10R of N1-ethyloxycarbonyl-N2-allyl-5-[3-(triisopropyloxy)propyl]indazolinone (16) on TIPS Using the Claisen Rearrangement To a solution of (10)(5 mg, 0.0106 mmol, 1.0 eq.) in dry THF (5 mL) was added a catalytic amount of tetrakis(triphenylphosphine). The reaction was stirred at room temperature for 16 hours under nitrogen. The solvent was removed in vacuo and the crude solid was purified by flash chromatography eluting with 0-10% ethyl acetate/petrol ether to give the desired product (16) as a colourless oil; $^1$H NMR data was identical to the product obtained by reaction of (9N) with tri(isopropyl)silyl triflate above.

Synthesis of N1-ethyloxycarbonyl-N2-allyl-5-[3-(triisopropyloxy)propyl]indazolinone on TIPS Poly TIPS Resin (16R) by Palladium Rearrangement of (10R)

Figure 2A:
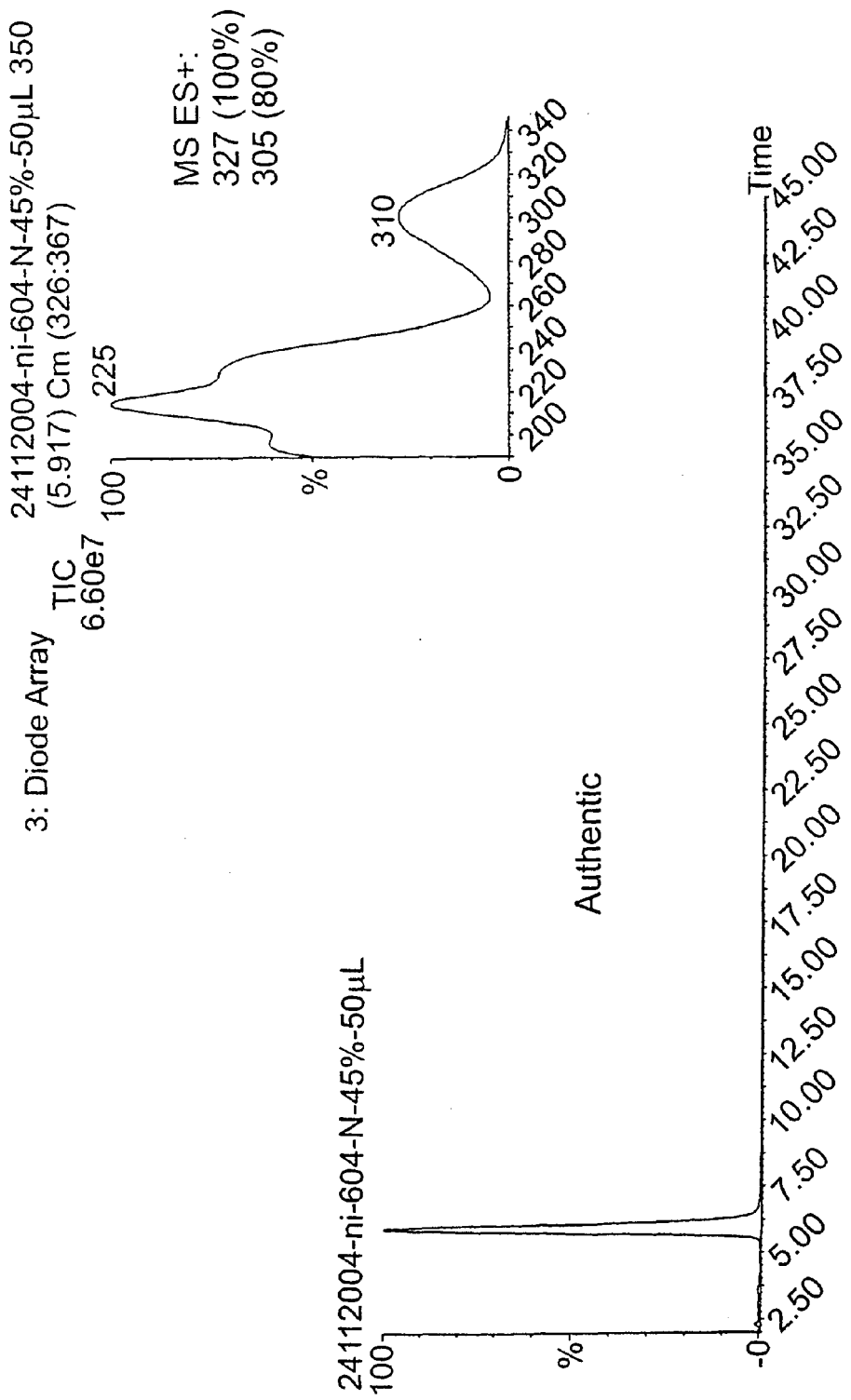
FIGS. 2a and 2b: Comparison by LC/MS of (9N)(top) and the product obtained by rearrangement with palladium on the resin 10R (bottom).
Figure 2B:
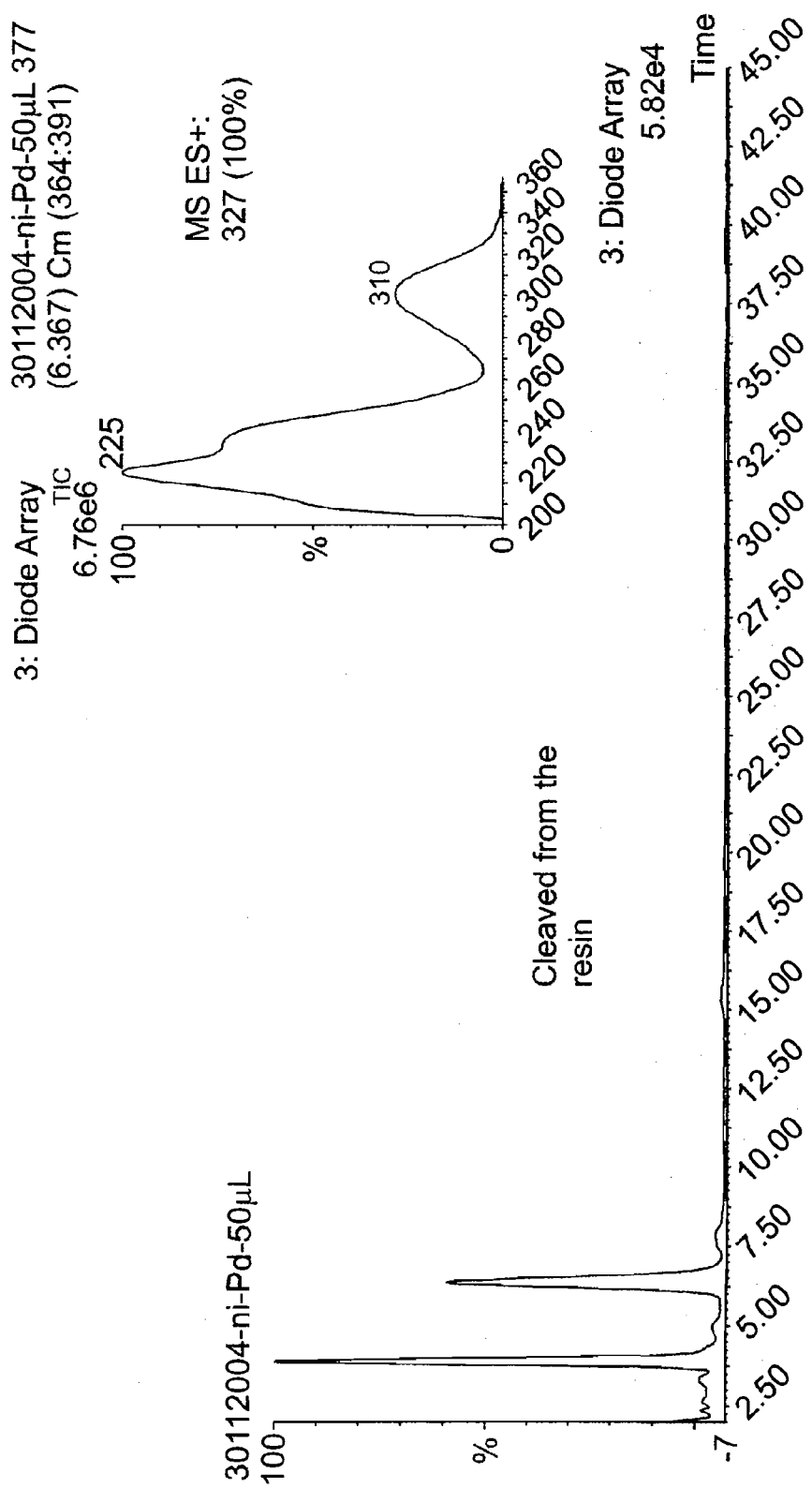

(10R)(9 mg) were dissolved in THF (2 mL) and palldium triphenylphosphine (1 mg) was added to the reaction mixture. The reaction was stirred for 16 hours at room temperature under inert atmosphere. The resin was submitted to the washing procedure and to the cleavage procedure. The products were compared by LC/MS to the authentic material (9N) previously prepared in solution (see FIGS. 2a and 2b).

Washing Procedure (Tallarico et al., 2001, J. Comb Chem 3:312-318):

The beads were drained, exposed to atmosphere and subjected to the following wash protocol: $CH_2Cl_2$ (2×3 mL×45 min.), THF (2×3 mL×30 min.), THF/IPA (3:1, 2×3 mL×30 min.), THF/$H_2O$ (3:1, 2×3 mL×30 min.), THF/IPA (3:1, 2×3 mL×30 min.), THF (2×3 mL×30 min.). The resin was air-dried for 1 hour and dried under vacuum.

Cleavage Procedure from the Solid Support:

Vacuum-dried resin was weighed (>5 mg) out into a solvent resistant scintillation vial and allowed to swell in 1.0 mL of THF for 30 min. The THF solution was removed and replaced with a fresh 0.95 mL of THF and 0.05 mL of HF/pyridine solution (7:3 ratio HF/pyridine, available from Aldrich Co). The vial was sealed and agitated for 3 h at which time 0.1 mL of methoxytrimethylsilane was added to quench unreacted HF. (Note: quench is mildly exothermic therefore use caution). The beads are further agitated for 30 minutes to ensure complete quenching. The solution was removed and the beads washed twice with additional 1.0 mL portions of fresh THF. All solvents were combined and concentrated in vacuo. The material recovered was then analysed by LC/MS and compared with the traces of authentic materials.

Figure 3A:
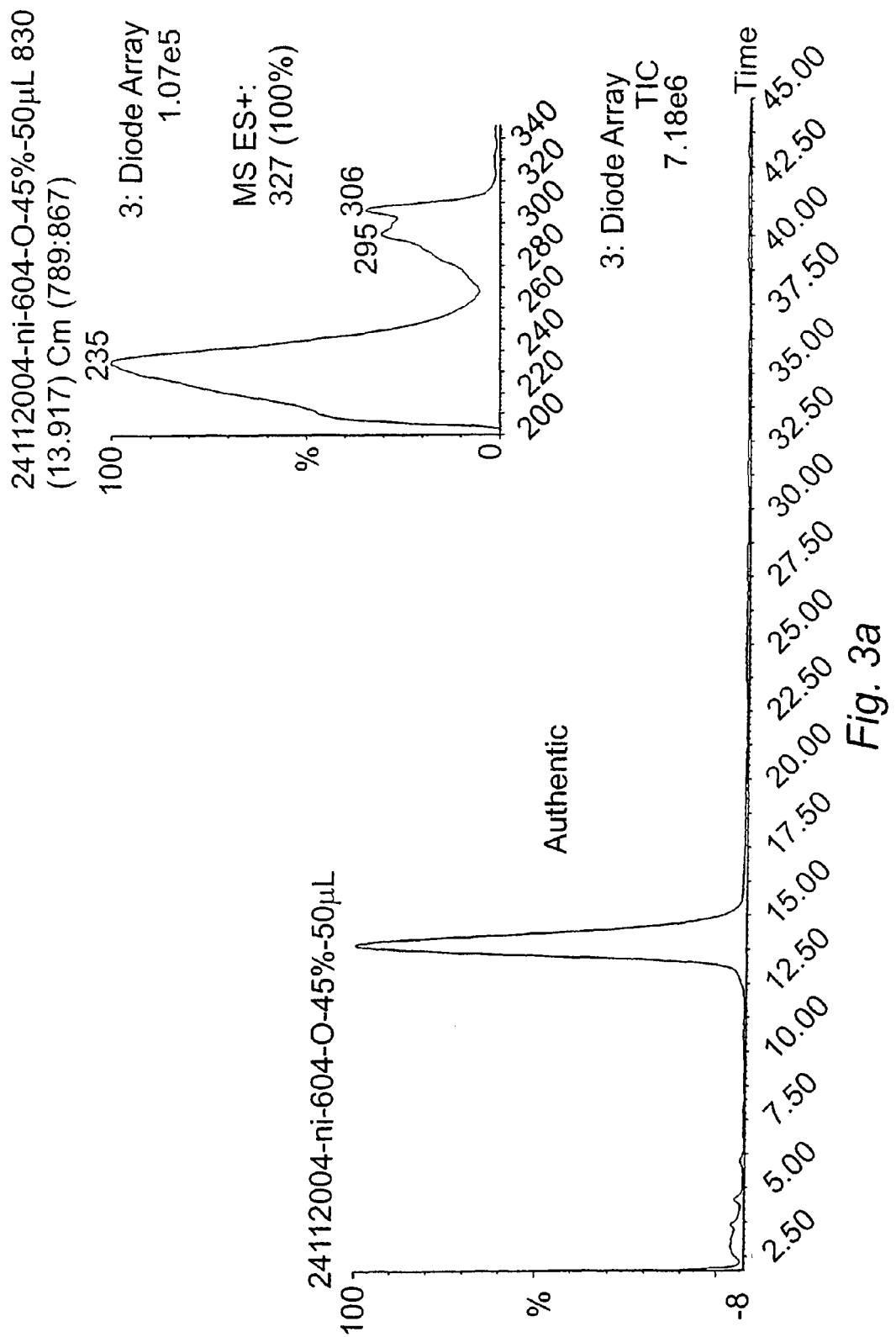
FIGS. 3a and 3b: Comparison by LC/MX of (9O) authentic material obtained by direct synthesis and the material cleaved off the resin (10R).
Figure 3B:
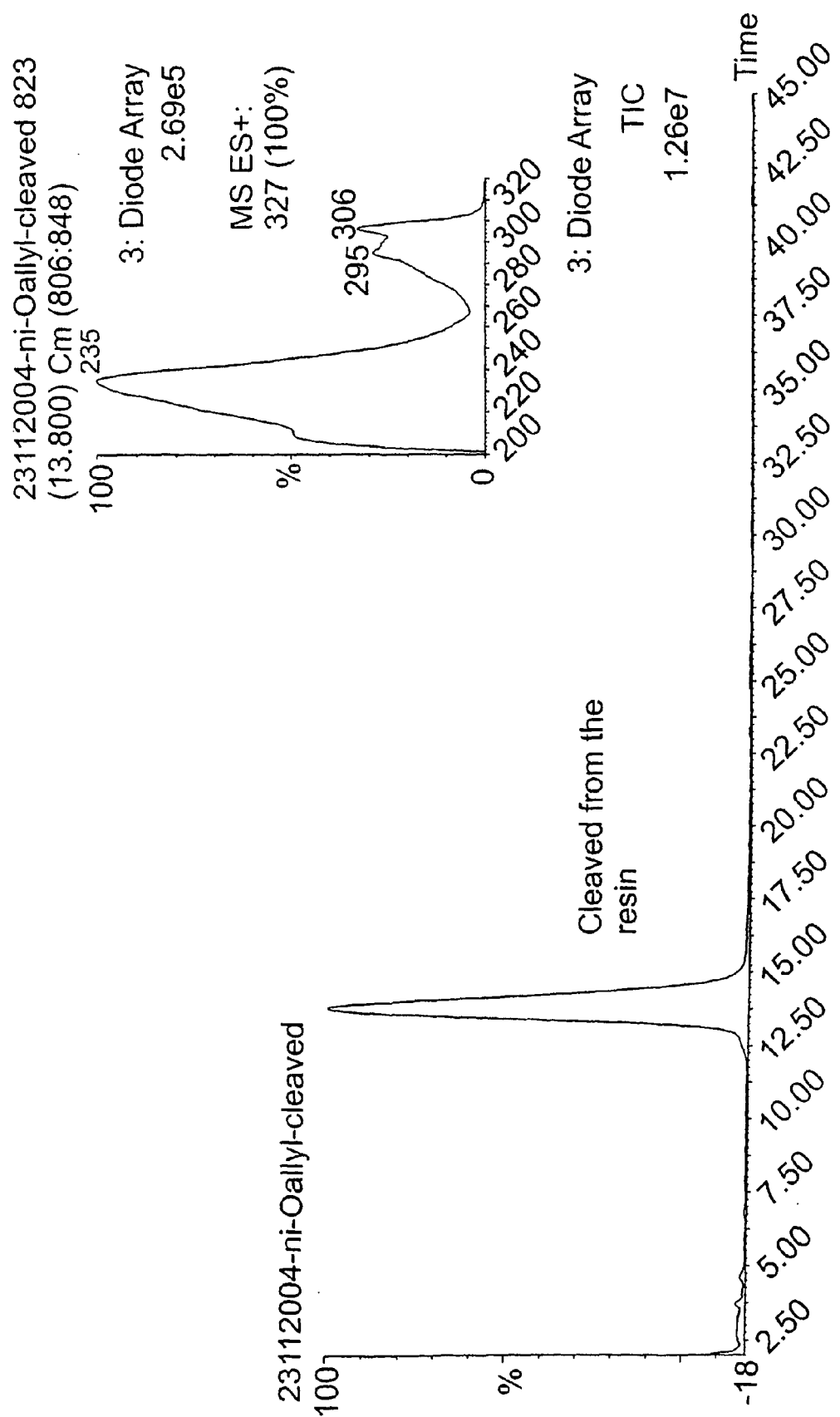

Proof of Loading of (9O) on Poly-TIPS Resin:

(10R) was submitted to the cleavage procedure and analysed by LC/MS and compared with (9O) previously prepared in solution (see FIGS. 3a and 3b).

Figure 4A:
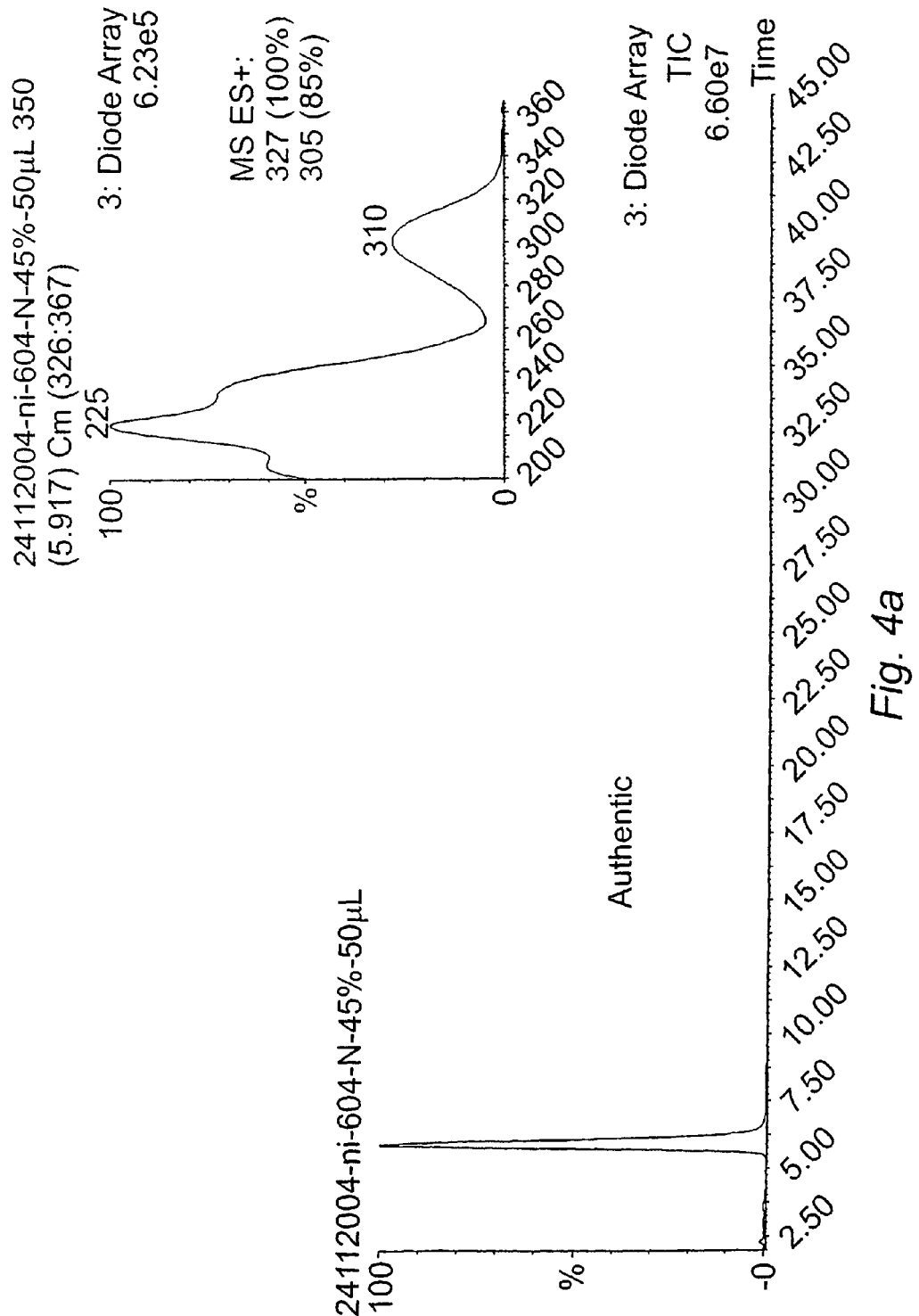
FIGS. 4a and 4b: Comparison by LC/MS of (9N) authentic material obtained by direct synthesis and the material cleaved off the resin (16R).
Figure 4B:
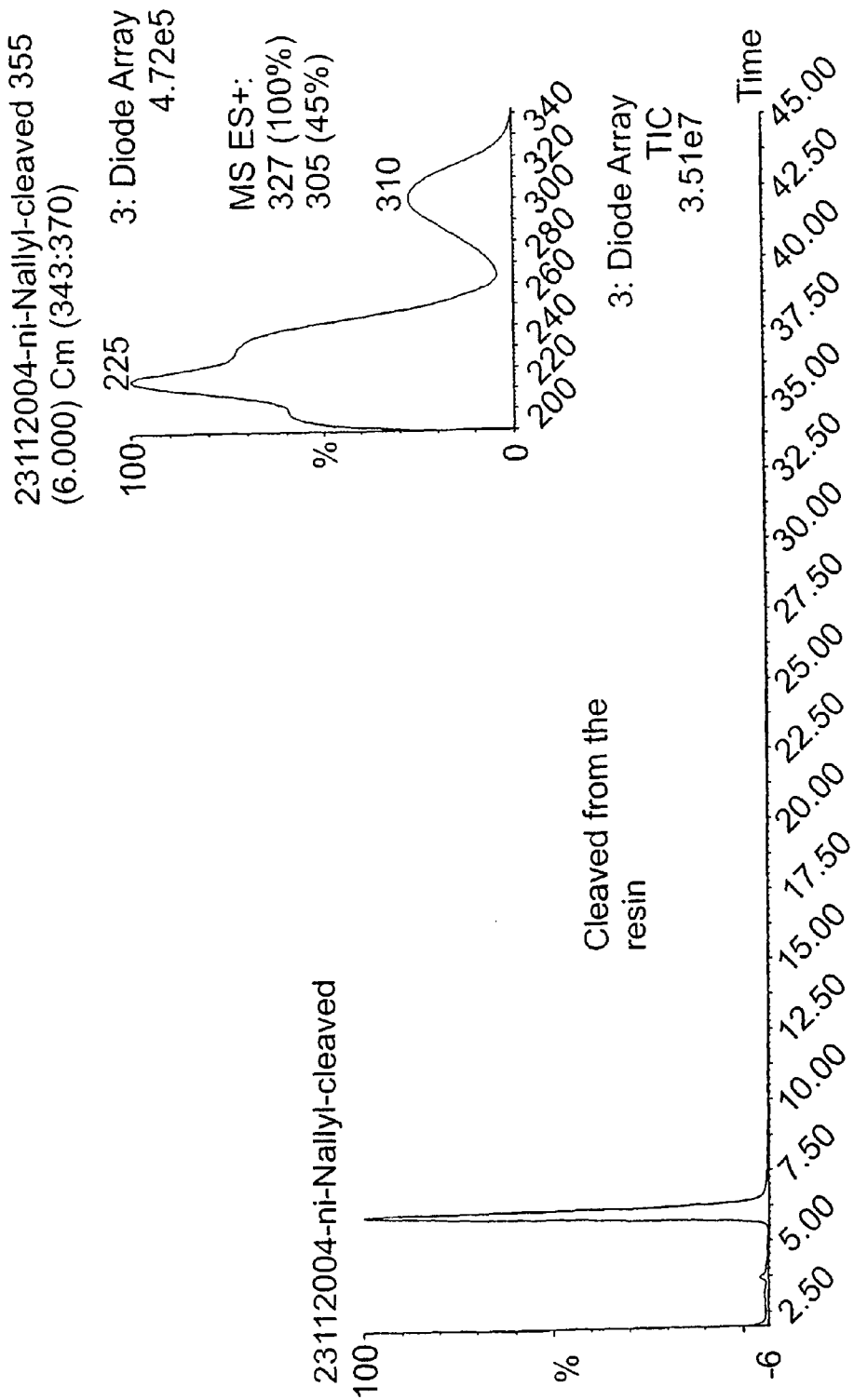

Proof of Loading of (9N) on the Poly-TIPS Resin:

(16R) was submitted to the cleavage procedure and analysed by LC/MS and compared with (9N) previously prepared in solution (see FIGS. 4a and 4b).

Synthesis of [O-allyl-5-[3-(triisopropylsilyloxy)propyl]indazolinone] (11) on TIPS Aqueous lithium hydroxide (2M, 2.0 mL) was added to a solution of (10)(57.0 mg, 0.12 mmol, 1.0 eq.) in THF (5 mL) and the reaction stirred vigorously for 16 hours at room temperature. The solvent was partially removed in vacuo. The reaction was then neutralised with dilute hydrochloric acid solution (10%) to pH 7 and extracted with ethyl acetate (3×25 mL). The combined organic extracts were dried ($MgSO_4$), and concentrated in vacuo. The crude material was purified by flash chromatography eluting with 10% ethyl acetate/hexane to give the desired product (11) as a colourless oil (36 mg, 0.09 mmol, 75%).

$^1$H NMR δ 8.74 (br s, 1 H; NH), 7.34 (s, 1H; Ar—H), 7.07 (d, J=1.5 Hz, 1H; Ar—H), 7.06 (d, J=0.9 Hz, 1 H; Ar—H), 6.00 (ddt, J=17.2, 10.5, 5.4 Hz, 1 H; C$\underline{H}$=$CH_2$), 5.31 (ddt, J=17.2, 1.5, 1.5 Hz, 1 H; CH=C$\underline{H}_{trans}$), 5.14 (ddt, J=10.5, 1.5, 1.5 Hz, 1 H; CH=C$\underline{H}_{cis}$), 4.75 (dt, J=5.4, 1.5 Hz, 2 H; C$\underline{H}_2$CH), 3.55 (t, J=6.2 Hz, 2 H; OC$\underline{H}_2$$CH_2$), 2.63 (m, 2 H; ArC$\underline{H}_2$$CH_2$), 1.72 (m, 2 H; ArC$\underline{H}_2$$CH_2$), 0.92-0.88 (m, 21 H; H$_{tips}$).

Synthesis of [O-allyl-5-[3-(triisopropylsilyloxy)propyl]indazolinone] (11H)

To a solution of (11)(23.0 mg, 0.059 mmol, 1.0 equiv.) in THF (5 mL) was added tetrabutyl ammonium fluoride (TBAF)(30 mg, 0.12 mmol, 2.00 equiv.) and the mixture was stirred at room temperature for 16 hours. The reaction mixture was then quenched by addition of ammonium chloride (5 mL) and extracted with ethyl acetate (3×5 mL). The combined organic extracts were dried ($MgSO_4$), concentrated in vacuo. The crude material was purified by flash chromatography eluting with 40% ethyl acetate/hexane to give the desired product (11H) as a yellow oil (9.00 mg, 66%); Rf (50% ethyl acetate/petrol) 0.16; $^1$H NMR δ 8.90 (br s, 1H; NH), 7.44 (s, 1H; H-4), 7.16 (d, J=1.6 Hz, 2H; H-6, H-7), 6.11 (ddt, J=17.2, 16.0, 5.5 Hz, 1H; H-10), 5.41 (dq, J=17.2, 1.6 Hz, 1H; H-11a), 5.25 (dq, J=10.5, 1.3 Hz, 1H; H-11b), 4.84 (dt, J=5.5, 1.4 Hz, 2H; H-9), 3.62 (t, J=6.4 Hz, 2H; H-14), 2.73 (m, 2H; H-12), 1.86 (m, 2H; H-13), 1.63 (br s, 1H; OH); $^{13}$C NMR δ 157.0 (C-3), 141.5 (C-7a), 133.4 (C-10), 133.1 (C-5), 128.2 (C-6), 118.5 (C-4), 117.9 (C-11), 112.9 (C-3a), 109.6 (C-7), 69.5 (C-9), 62.1 (C-14), 34.5 (C-12), 31.8 (C-13); LR MS (ES$^+$) m/z: 255 [M+Na]$^+$, HR MS (ES$^+$) calcd for $C_{13}H_{16}N_2O_2Na$ [M+Na]$^+$: 255.1109, found 255.1105; IR (thin film, cm$^{-1}$) 3256 br, 2928 stg, 2852 m, 1529 stg, 1499 stg, 1458 m, 1324 stg, 1253 m, 1207 m, 983 stg, 929 m, 766 m.

Synthesis of [O-allyl-5-[3-(triisopropylsilyloxy)propyl]indazolinone] on Poly TIPS Resin (11R)

Figure 5A:
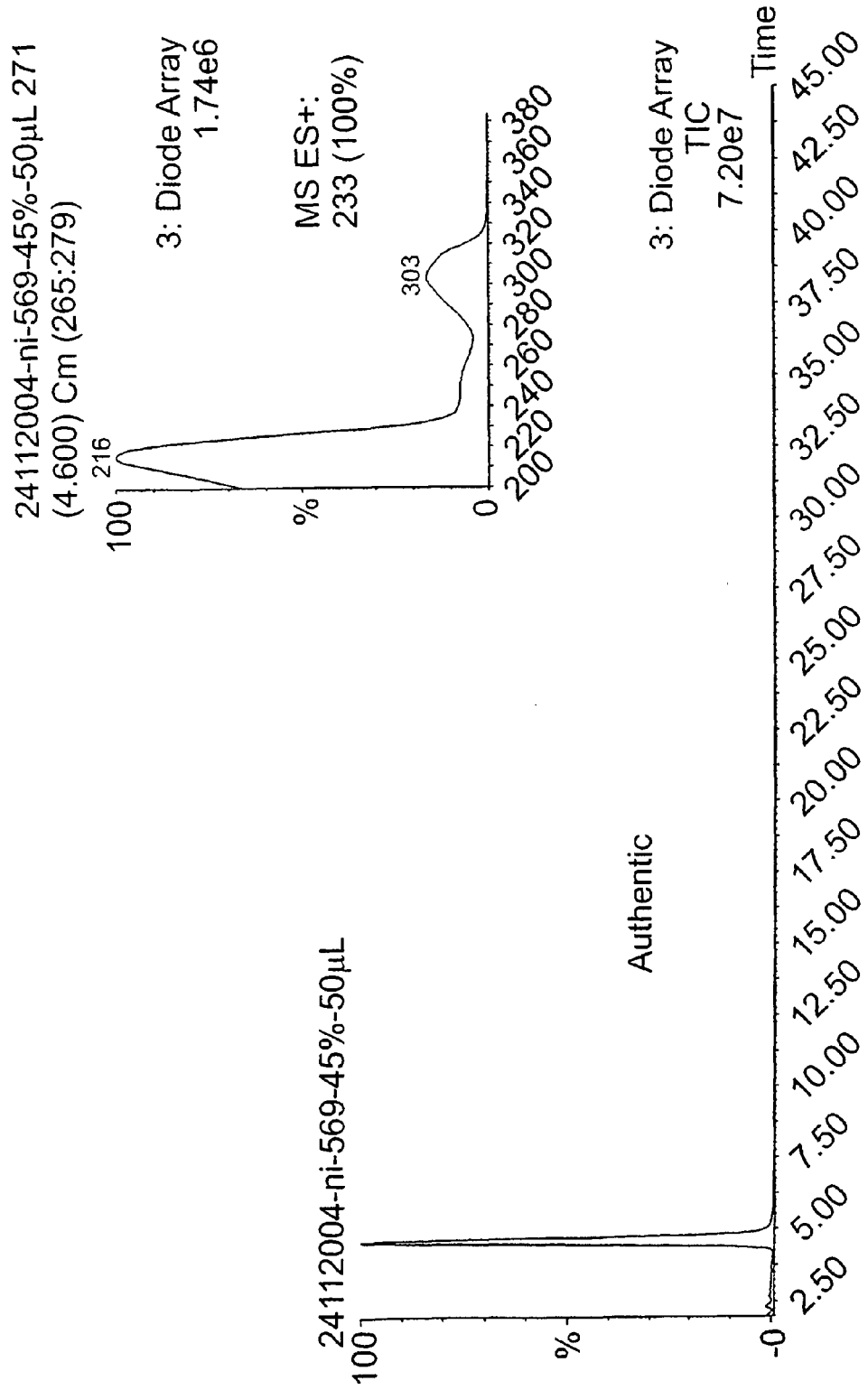
FIGS. 5a and 5b: Comparison by LC/MS of (11H) authentic material obtained by direct synthesis and the material cleaved off the resin (10R).
Figure 5B:
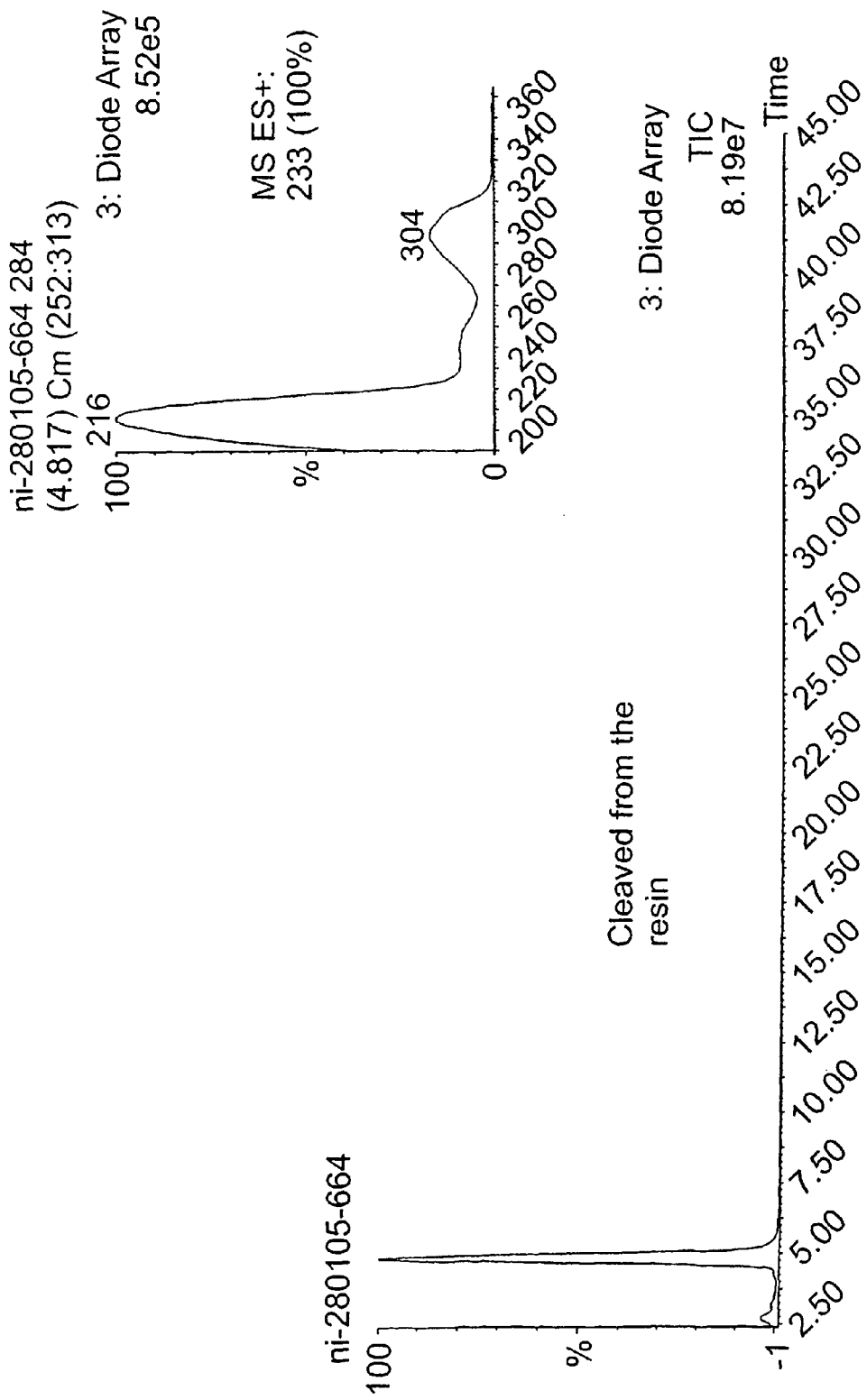

10R (30 mg) were reacted for 2 days at 50° C. in a solution of THF (3 mL) and lithium hydroxide 2 M (400 μL). The beads were submitted to the cleavage conditions and the solution was analysed by LC/MS and compared with (11H) prepared in solution (see FIGS. 5a and 5b).

Synthesis of N1-benzyl-O-allyl 5-[3-(triisopropyloxy)propyl]indazolinone on TIPS (12)

To a solution of (11)(36 mg, 0.09 mmol, 1.0 eq.) in dry THF (5 mL) was added potassium tert-butoxide (20 mg, 0.18 mmol, 2.0 eq.) and benzyl bromide (0.02 mL, 0.14 mmol, 1.5 eq.) under an inert atmosphere. The solution was stirred at room temperature for 30 minutes. The reaction was quenched by addition of saturated ammonium chloride solution (10 mL) and extracted with ethyl acetate (3×15 mL). The combined organic extracts were dried ($MgSO_4$) and concentrated in vacuo. The crude material was purified by flash chromatography eluting with 0 to 10% ethyl acetate/hexane to give the desired product (12) as a colourless oil (28 mg, 0.06 mmol, 67%).

$^1$H NMR δ 7.42-7.41 (m, 1H; Ar—H), 7.23-7.07 (m, 6 H; Ar—H), 7.00 (dd, J=8.7, 0.8 Hz, 1H; Ar—H), 6.09 (ddt, J=17.2, 10.5, 5.6 Hz, 1H; C$\underline{H}$=$CH_2$), 5.40 (ddt, J=17.2, 1.6, 1.6 Hz, 1H; CH=C$\underline{H}_{trans}$), 5.23 (s, 2H; PhC$\underline{H}_2$N), 5.22 (ddt, J=10.5, 1.6, 1.3 Hz, 1H; CH=C$\underline{H}_{cis}$), 4.83 (m, 2H; OC$\underline{H}_2$CH), 3.64 (t, J=6.3 Hz, 2H; OC$\underline{H}_2$$CH_2$), 2.69 (m, 2H; ArC$\underline{H}_2$$CH_2$), 1.79 (m, 2H; ArCH$_2$C$\underline{H}_2$), 0.99 (m, 21H; Si[C$\underline{H}_2$(C$\underline{H}_3$)$_2$]$_3$).

Synthesis of [N1-benzyl-O-allyl 5-[3-(hydroxy)propyl]indazolinone] (13) Through (12)

To a solution of (12)(47.0 mg, 0.10 mmol, 1.0 eq.) in dry THF (5 mL) was added tetrabutylammonium fluoride (55 mg, 0.20 mmol, 2.0 eq.) and the reaction mixture was stirred at room temperature for 16 hours. The reaction was quenched by addition of saturated ammonium chloride solution (10 mL) and extracted with ethyl acetate (3×15 mL). The combined organic extracts were dried ($MgSO_4$) and concentrated in vacuo. The crude material was purified by flash chromatography eluting with 20-100% ethyl acetate/hexane to give the desired product (13) as a colourless oil (30 mg, 0.09 mmol, 89%).

$^1$H NMR δ 7.41 (br s, 1H; Ar—H), 7.23-7.07 (m, 6H; Ar—H), 7.00 (br d, 1H; Ar—H), 6.09 (ddt, J=17.2, 10.4, 5.6 Hz, 1H; CH=$CH_2$), 5.40 (ddt, J=17.2, 1.6, 1.6 Hz, 1H; CH=C$H_{trans}$), 5.29 (s, 2H, PhC$H_2$N), 5.22 (ddt, J=10.4, 1.4, 1.4 Hz, 1H; CH=C$H_{cis}$), 4.83 (ddd, J=5.6, 1.4, 1.4 Hz, 2H; OC$H_2$CH), 3.60 (t, J=6.4 Hz, 2H; OC$H_2$C$H_2$), 2.73-2.68 (m, 2H; ArC$H_2$C$H_2$), 1.88-1.79 (m, 2H; ArCH$_2$C$H_2$).

Figure 6A:
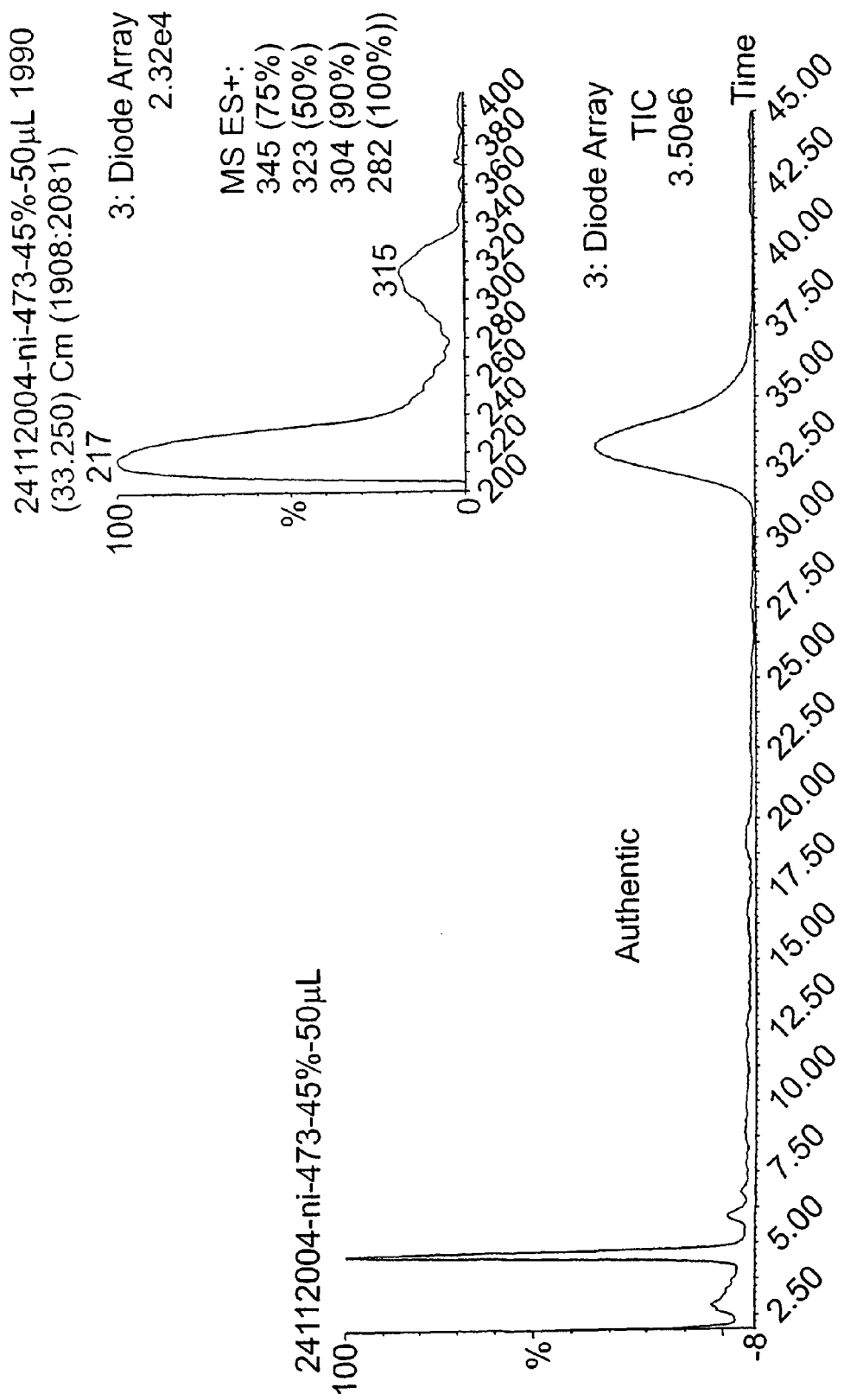
FIGS. 6a and 6b: Comparison by LC/MS of (13) authentic material obtained by direct synthesis and the material cleaved off the resin (12R).
Figure 6B:
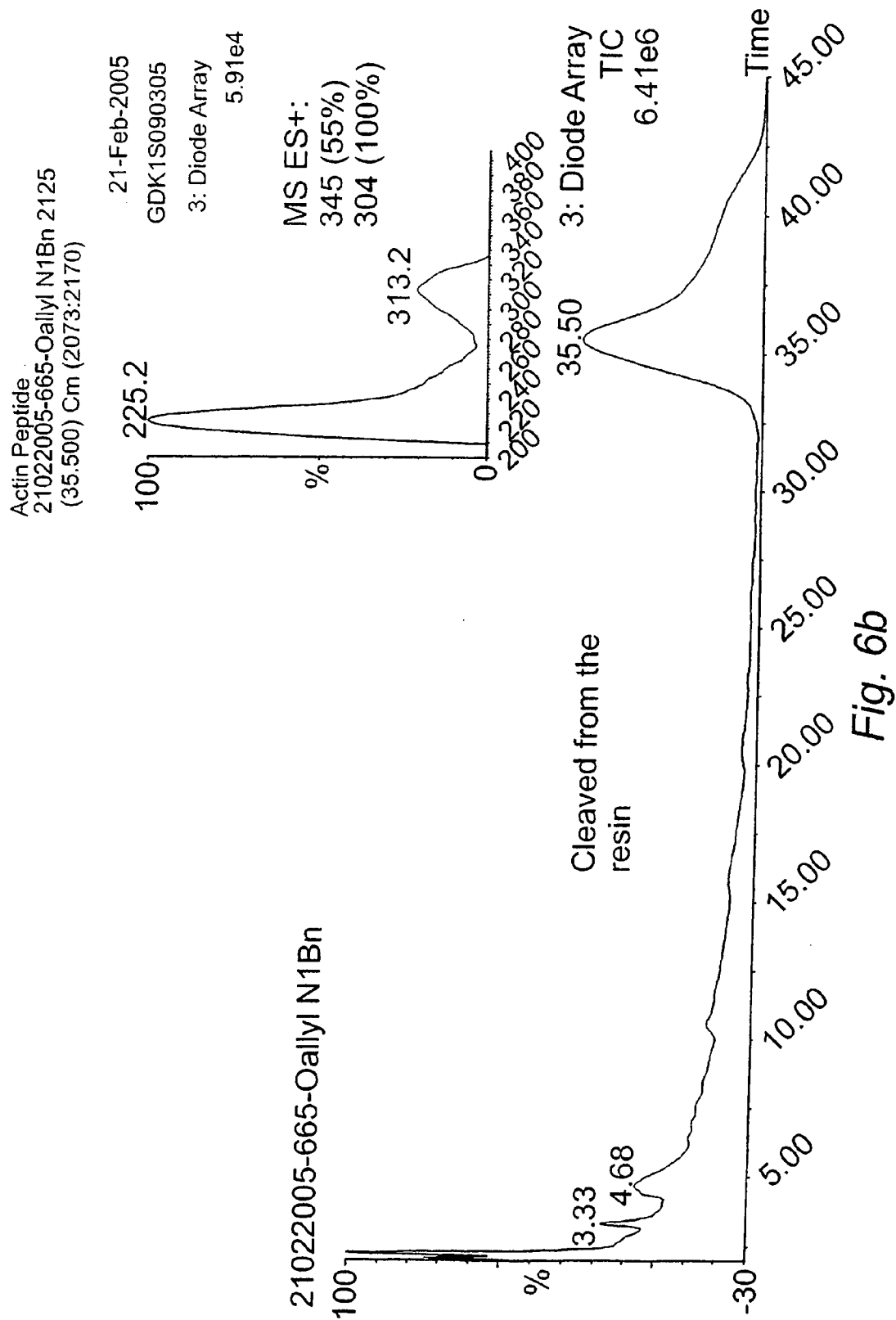

Synthesis of [N1-benzyl-O-allyl 5-[3-(hydroxy)propyl]indazolinone] (13) Through 12R (11R)(26 mg) were reacted with an excess of benzyl bromide (100 μL) in presence of excess of potassium t-butoxide (20 mg) in THF (3 mL). The reaction was stirred at room temperature for 4 days. The resin was washed according to the standard procedure and submitted to the cleavage procedure previously described. The solution was compared with (13) prepared in solution by LC/MS (see FIGS. 6a and 6b).

Synthesis of [N2-allyl-5-[3-(triisopropylhydroxy)propyl]indazolinone] on TIPS (17)

To a solution of (16)(80 mg, 0.17 mmol, 1.0 eq.) in THF (10 mL) was added an aqueous lithium hydroxide solution (2M, 2.0 mL, 4.0 mmol, 4.0 eq.). The reaction mixture was stirred vigorously at room temperature for 16 hours. The reaction was then neutralised with diluted hydrochloric acid solution (10%) to pH 7 and extracted with ethyl acetate (3×15 mL). The combined organic extracts were dried ($MgSO_4$) and concentrated in vacuo. The crude material was purified by flash chromatography eluting with 30% ethyl acetate/hexane to give the desired product (17) as a colourless oil (44 mg, 0.11 mmol, 65%).

1H NMR δ 7.56 (br s, 1H; Ar—H), 7.39 (s, 1H; OH), 7.29 (dd, J=8.4, 1.7 Hz, 1H; Ar—H), 7.06 (d, J=8.4 Hz, 1H; Ar—H), 5.82 (m, 1H; CH=$CH_2$), 5.27-5.18 (m, 2H, CH=C$H_2$), 4.40 (m, 2H; NC$H_2$CH), 3.63 (t, J=6.2 Hz, 2H; OC$H_2$C$H_2$), 2.69 (m, 2H; ArC$H_2$C$H_2$), 1.78 (m, 2H, ArCH$_2$C$H_2$), 0.98 (m, 21H; Si[C$H_2$(C$H_3$)$_2$]$_3$); $^{13}$C NMR δ 162.5, 145.4, 137.1, 133.0, 131.9, 122.8, 119.5, 119.3, 112.3, 62.3, 46.7, 34.8, 31.7, 18.0, 11.9; HMBC and HMQC are consistent with the proposed structure (17).

Synthesis of [N2-allyl-5-[3-(triisopropylhydroxy)propyl]indazolinone] (17H)

To a solution of (16)(20.0 mg, 0.052 mmol) in THF (5 mL) was added tetrabutylammonium fluoride (27.0 mg, 0.10 mmol, 2.0 equiv.). The reaction mixture was stirred for 16 hours at room temperature. The reaction was quenched by addition of saturated solution of ammonium chloride and extracted with ethyl acetate (3×10 mL). The combined organic extracts were dried ($MgSO_4$), concentrated in vacuo. The crude product was purified by flash chromatography eluting with ethyl acetate to afford the desired compound (17H) as a yellow oil (7 mg, 60%); Rf (ethyl acetate) 0.06; $^1$H NMR δ 7.57 (s, 1H; H-4), 7.30 (dd, J=8.5, 1.3 Hz, 1H; H-6), 7.08 (d, J=8.3 Hz, 1H; H-7), 5.86 (ddt, J=16.3, 10.1, 6.2 Hz, 1H; H-9), 5.29 (br d, J=11.8 Hz, 1H; H-10), 5.25 (br d, J=5.4 Hz, 1H; H-10), 4.44 (d, J=6.0 Hz, 2H; H-8), 3.59 (t, J=6.3 Hz, 2H; H-13), 2.71 (t, J=7.6 Hz, 2H; H-11), 1.82 (m, 2H; H-12), 1.72 (br s, 2H; NH and OH); $^{13}$C NMR δ 145.5 (C-3), 136.8 (C-5), 132.9 (C-6), 131.8 (C-9), 122.9 (C-4), 119.6 (C-10), 112.5 (C-7), 100.2 (C-quat.), 61.8 (C-13), 46.8 (C-8), 34.2 (C-12), 31.5 (C-11), one C-quat. missing on the spectrum; LR MS (CI$^+$) m/z: 233 [M+H]$^+$, HR MS (CI$^+$) calcd for $C_{13}H_{17}N_2O_2$ [M+H]$^+$: 233.1290, found 233.1288; IR (thin film, cm$^{-1}$) 2928 stg, 2856 stg, 1627 stg (C=N), 1496 m (C=N), 1457 m, 1058 w;

Synthesis of [N2-allyl-5-[3-(triisopropylhydroxy)propyl]indazolinone] on Poly Resin TIPS (17R)

Figure 7A:
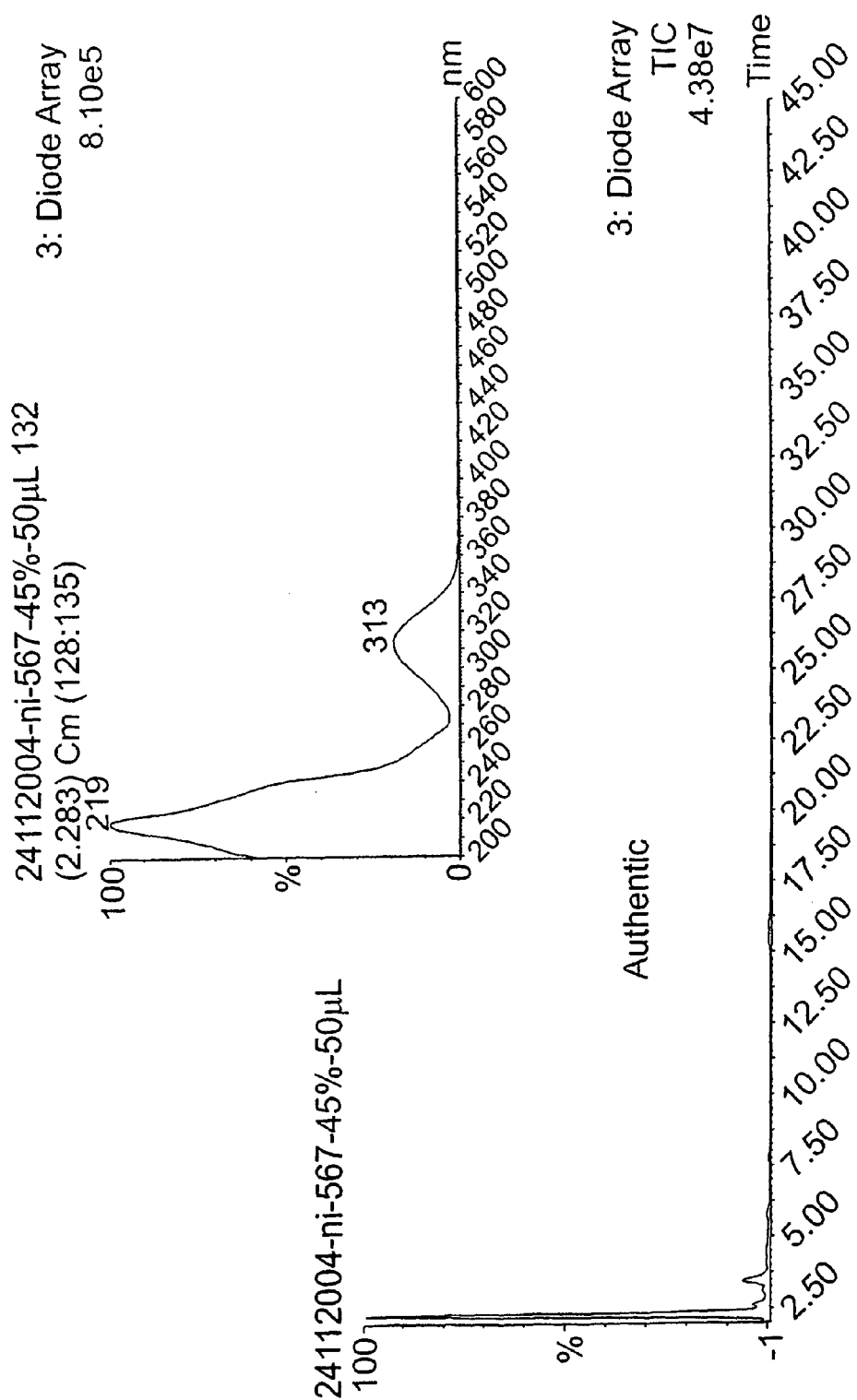
FIGS. 7a to 7d: Comparison by LC/MS of (17H) authentic material obtained by direct synthesis and the material cleaved off the resin (16R) after treatment with lithium hydroxide.
Figure 7B:
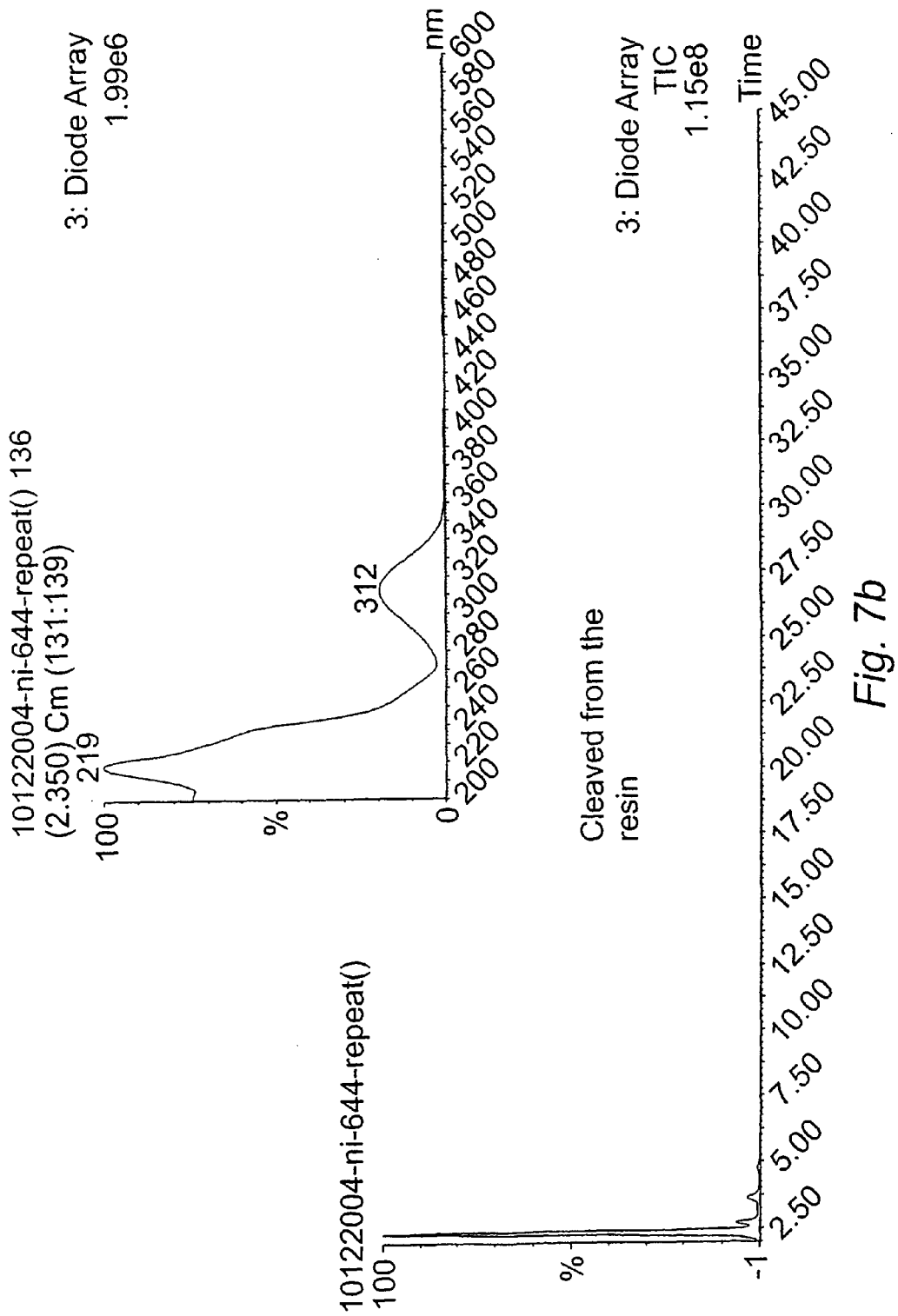
Figure 7C:
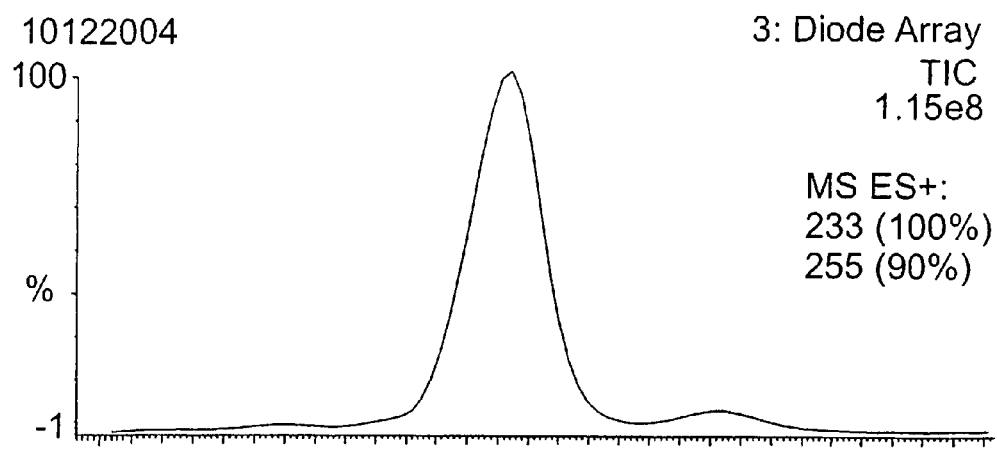
Figure 7D:
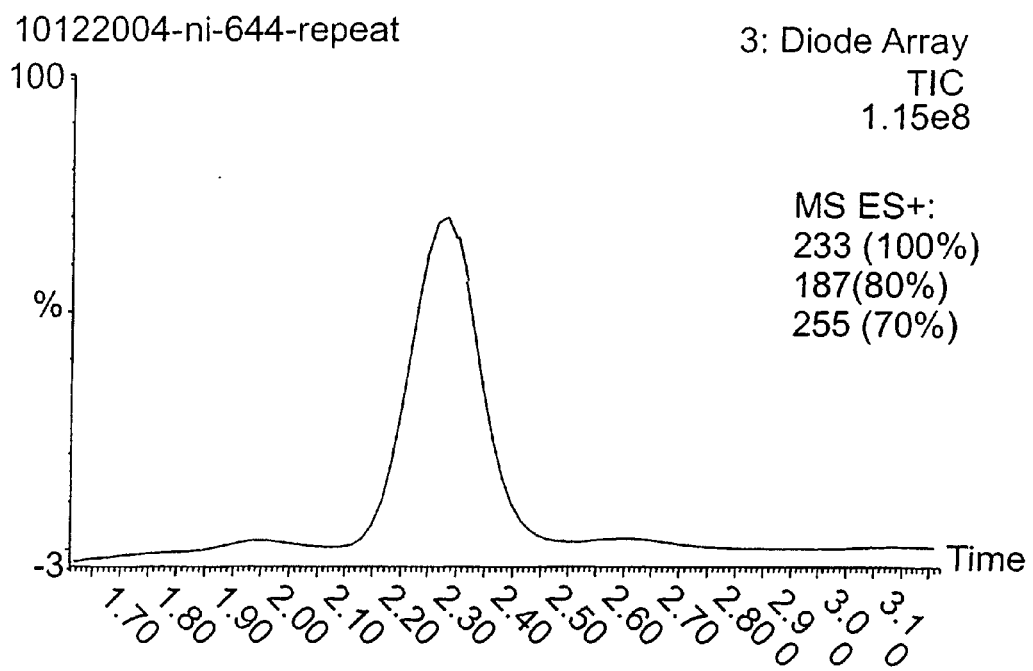

(16R)(10 mg) were reacted with a solution (2 mL) of LiOH (2 M) in THF (1:15, v/v) at room temperature for 16 hours. The resin was washed according to the washing procedure and the products were cleaved following the cleavage procedure. The solution was compared to (17H) previously prepared in solution by LC/MS (see FIGS. 7a and 7b).

Synthesis of [N1-benzyl-N2-allyl-5-(3-hydroxypropyl) indazolinone] (15) Through (14) by Rearrangement of (12) Using Tetralis

Synthesis of [N1-benzyl-N2-allyl-5-[3-(triisopropyloxy)propyl]indazolinone] (14) on TIPS To a solution of (12)(20.0 mg, 0.04 mmol, 1 eq.) in dry THF (5 mL) was added tetrakis (triphenylphosphine) palladium (10 mg, 8.66×10$^6$ mol, 20% mol.). The solution was stirred at room temperature under an inert atmosphere in a flask protected with foil for 16 hours. The reaction was quenched with addition of ammonium chloride (5 mL) and extracted with ethyl acetate (3×15 mL). The combined organic extracts were dried ($MgSO_4$) and concentrated in vacuo. The product was purified by flash chromatography eluting with hexane to afford (14) as a colourless oil (18.0 mg, 0.04 mmol, 90%).

$^1$H NMR δ 7.58 (s,1H; Ar—H), 7.29-6.94 (m, 7H; Ar—H), 5.73 (m, 1H; NC$H_2$CH=); 5.14 (m, 1H; CH=C$H_2$); 5.10 (m, 1H; CH=C$H_2$); 4.71 (s, 2H; NC$H_2$Ph); 4.43 (dt, J=5.7, 1.4 Hz, 2H; NC$H_2$CH); 3.63 (t, J=6.2 Hz, 2H; OC$H_2$C$H_2$); 2.69 (m, 2H; C$H_2$C$H_2$Ar); 1.79 (m, 2H; C$H_2$CH$_2$Ar); 0.99 (m, 21H; Si[C$H_2$(C$H_3$)$_2$]$_3$).

Synthesis of N1-benzyl-N2-allyl-5-(3-hydroxypropyl)indazolinone (15)

To a solution of (14)(2 mg, 0.0042 mmol, 1 eq.) in dry THF (10 mL) was added tetrabutylammonium fluoride solid (5 mg, 0.023 mmol, 5 eq.). The reaction mixture was stirred at room temperature under an inert atmosphere for 16 hours. The reaction was quenched by addition of ammonium chloride (15 mL) and extracted with ethyl acetate (3×15 mL). The combined organic extracts were dried (MgSO$_4$) and concentrated in vacuo. The product was purified by flash chromatography eluting with ethyl acetate to give (15) as a colourless oil.

$^1$H NMR δ 7.59 (s, 1H; Ar—H); 7.28-6.95 (m, 7H; Ar—H); 5.75 (m, 1H; NCH$_2$C$\underline{H}$); 5.12 (m, 2H; CH=C$\underline{H}_2$); 4.71 (s, 2H; NC$\underline{H}_2$Ph); 4.44 (d, J=5.6 Hz, 2H; NC$\underline{H}_2$CH); 3.60 (t, J=6.3 Hz, 2H; OC$\underline{H}_2$CH$_2$); 2.70 (t, J=7.6 Hz, 2H; CH$_2$C$\underline{H}_2$Ar); 1.83 (m, 2H; C$\underline{H}_2$CH$_2$Ar).

Figure 9A:
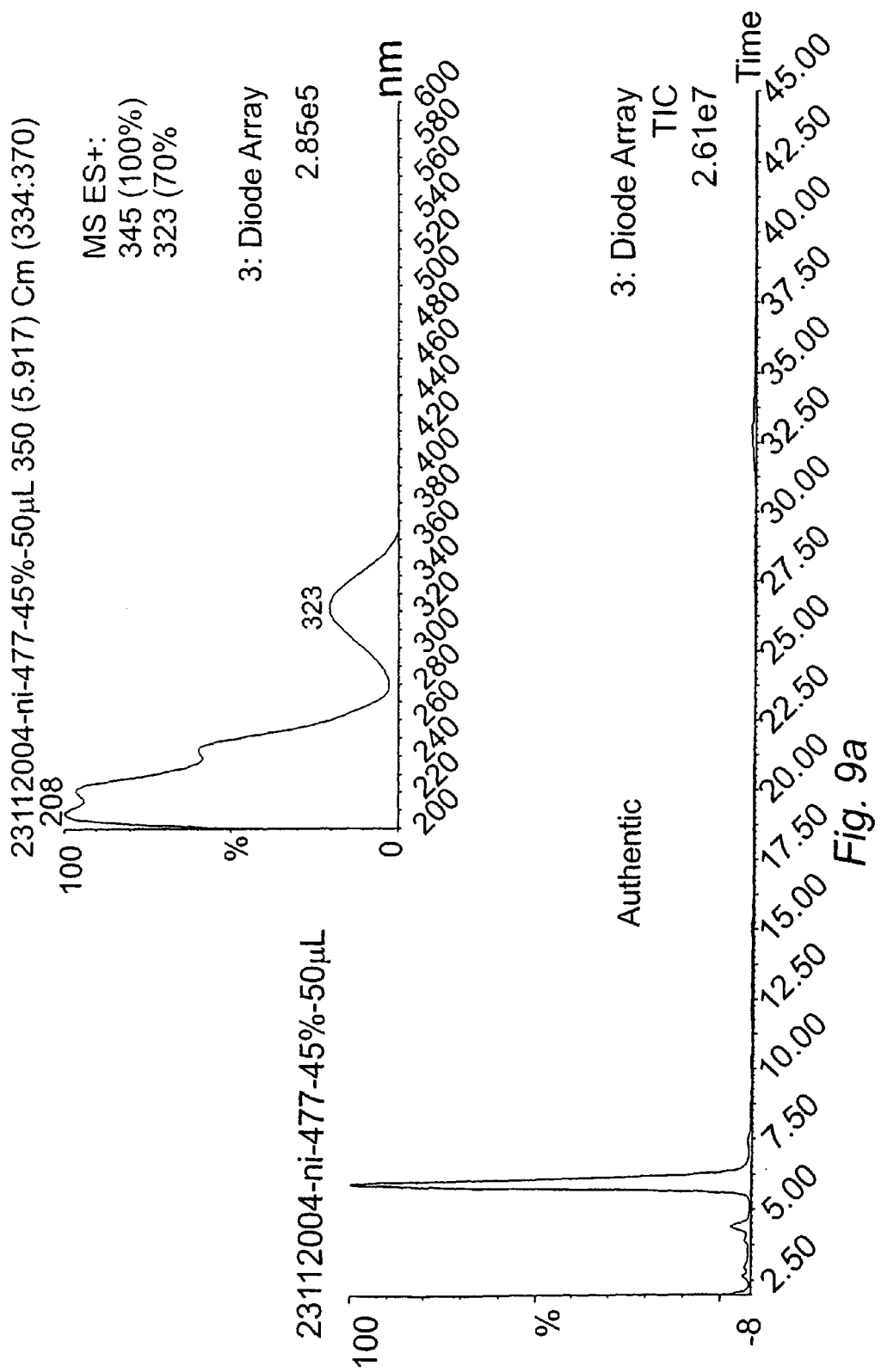
FIGS. 9a and 9b: Comparison by LC/MS of (15) authentic material made in solution (top) and the product obtained by rearrangement of (12R) with microwave (bottom).
Figure 9B:
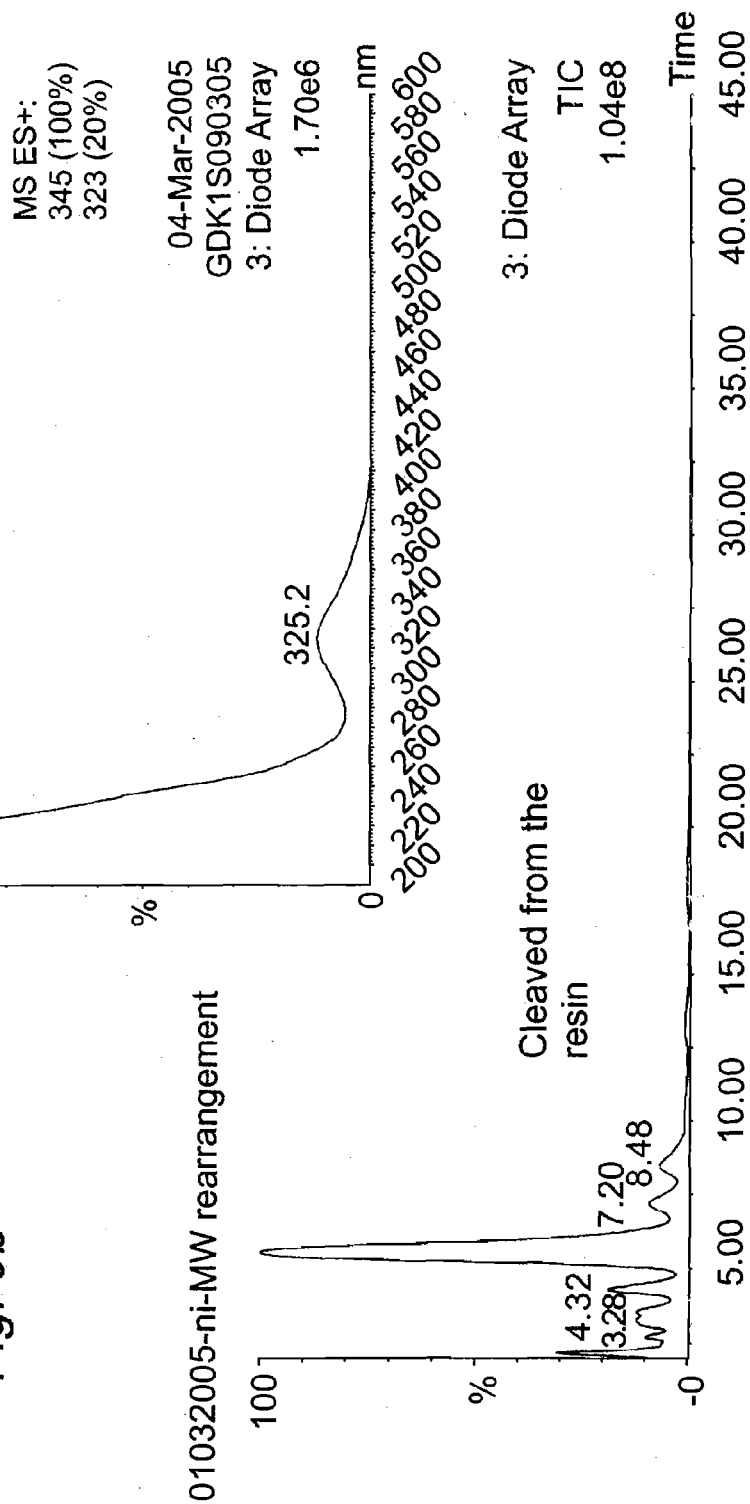

Synthesis of [N1-benzyl-N2-allyl-5-(3-hydroxypropyl)indazolinone] (15) Through (14R) by Rearrangement of (12R) Using Microwave Radiation (12R)(5 mg) were heated for 30 minutes at 200° C. in DMF (1 mL). The resin was washing according to the washing procedure and the material was cleaved following the cleavage procedure. The remaining product was compared by LC/MS to (15) previously prepared in solution (see FIGS. 9a and 9b).

Synthesis of [N1-benzyl-N2-allyl-5-(3-hydroxypropyl)indazolinone] (15) Through (14R) by Alkylation of (17R)

Figure 8A:
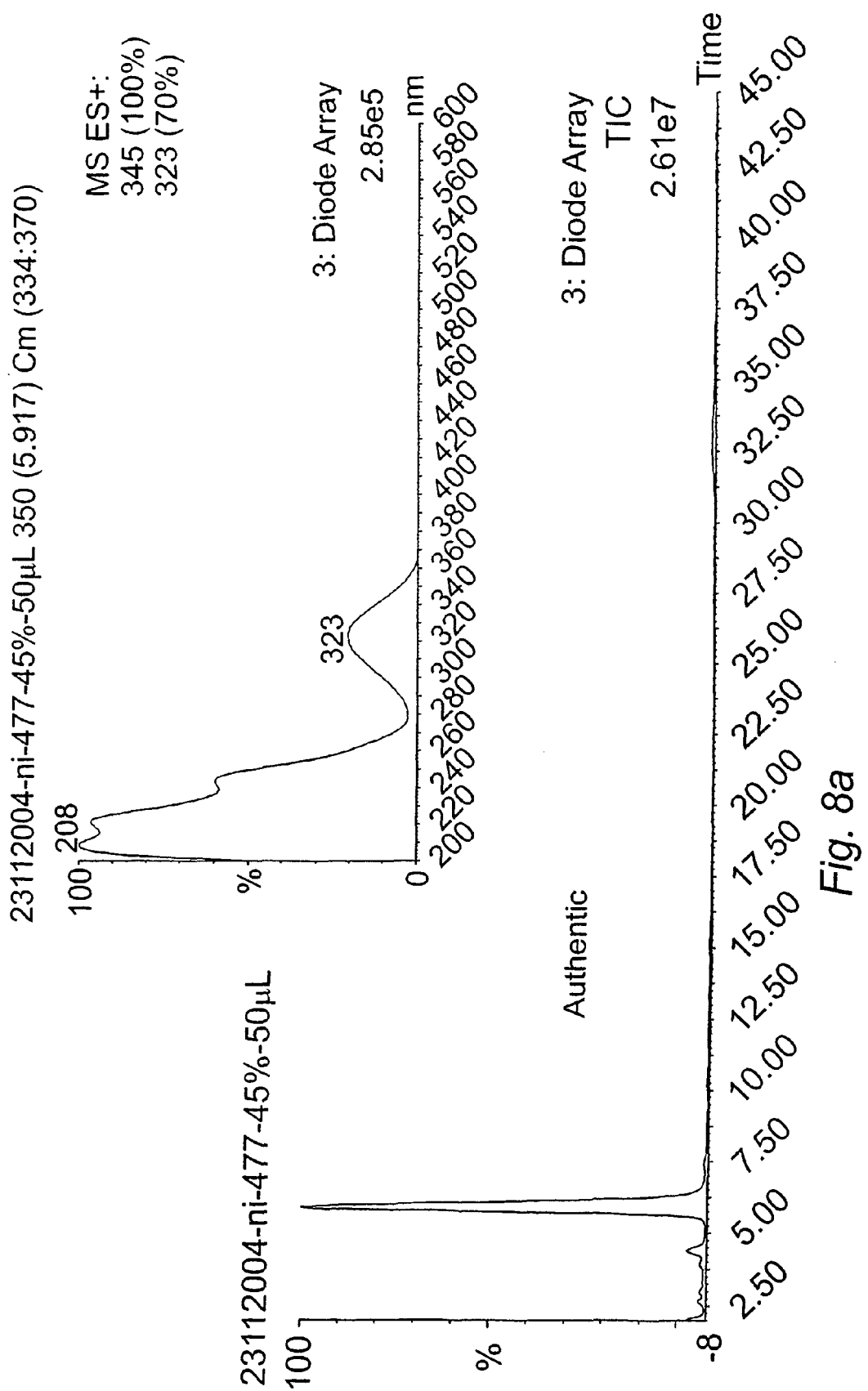
FIGS. 8a and 8b: Comparison by LC/MS of (15) authentic material obtained by direct synthesis and the material cleaved off the resin (17R).
Figure 8B:
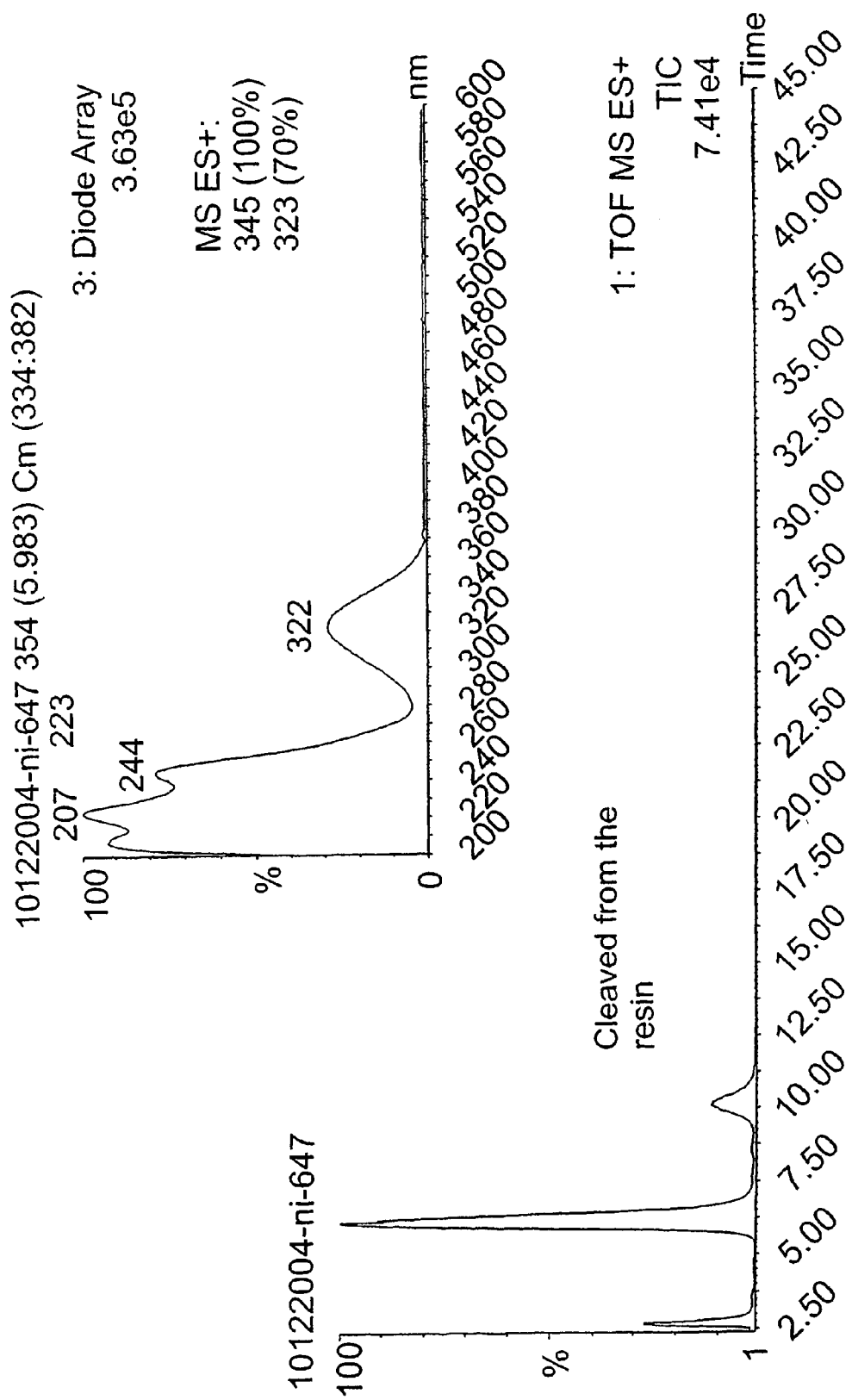

(17R)(4 mg) was reacted with excess of benzyl bromide (50 μL) and potassium t-butoxide (30 mg) in THF (3 mL). The reaction was stirred overnight at room temperature. The resin was subjected to the washing procedure and to the cleavage procedure. The solution was compared to (15) previously prepared in solution by LC/MS (see FIG. 8).

Example 9

TABLE 1

R groups introduced on the N1 position in the allyloxyindazole system

| Reagents | | | | |
|---|---|---|---|---|
| Br-CH$_2$Ph | Cl-C(O)Ph | O=C=N-Ph | Cl-SO$_2$-Ph | epoxide (±) |

| Substituent | | | | |
|---|---|---|---|---|
| (41) benzyl | (42) benzoyl | (43) HN-C(O)-Ph | (44) SO$_2$-Ph | (45) CH$_2$CH(OH)CH$_3$ (±) |

| Yield | | | | |
|---|---|---|---|---|
| 99% | 40% | 89% | 99% | 65% |

Synthesis of 41:

To a solution of 46 (100 mg, 0.58 mmol, 1.0 equiv.) in dry THF (10 mL) was added potassium carbonate (87.0 mg, 0.63 mmol, 1.1 equiv.), the solution was stirred at room temperature under an inert atmosphere for 30 minutes. Benzyl bromide (75 µL, 0.63 mmol, 1.1 equiv.) was added to the solution and the reaction was stirred overnight at room temperature under an inert atmosphere. The reaction was quenched by addition of ammonium chloride and extracted with ethyl acetate (3×50 mL). The combined organic extracts were dried (MgSO$_4$) and concentrated in vacuo. The crude material was purified by flash chromatography eluting with 5% ethyl acetate/petrol to afford 21 (90.0 mg) as a yellow oil in 99% yield based on recovered starting material (41.0 mg)(60% conversion, 40% of starting material recovered); R$_f$ (20% ethyl acetate/petrol) 0.47; $^1$H NMR δ 7.60 (dd, J=8.1, 0.6 Hz, 1H; H-4), 7.15 (m, 8H; H-aromatic), 6.94 (m, 1H; H-5), 6.08 (m, 1H; H-17), 5.38 (dt, J=17.2, 1.3 Hz, 1H; H-18a), 5.30 (S, 1H; H-8), 5.21 (br dt, J=10.4 Hz, 1H; H-18b), 4.83 (dd, J=5.6, 1.2 Hz, 2H; H-16); $^{13}$C NMR δ 155.6 (C-3), 141.6 (C-7a), 137.4 (C-9), 133.2 (C-17), 128.5 (C-aromatic), 127.4 (C-aromatic), 127.3 (C-aromatic), 126.9 (C-aromatic), 120.1 (C-4), 119.1 (C-5), 117.8 (C-18), 113.0 (C-3a), 108.8 (C-7), 69.6 (C-16), 52.3 (C-8); LR MS (CI$^+$) m/z: 265 [M+H]$^+$; HR MS (CI$^+$) calcd for C$_{17}$H$_{17}$N$_2$O [M+H]$^+$: 265.1341; found 265.1340; IR (thin film, cm$^{-1}$) 3060 m (C—H), 3030 m, 2924 m, 2852 m, 1615 m, 1527 stg (C=N), 1494 m (C=N), 1444 m, 1342 m, 1187 m, 1144 m;

Synthesis of 42:

To a solution of 46 (100 mg, 0.57 mmol) in dry THF (5 mL) was added triethylamine (88.0 µL, 0.63 mmol, 1.1 equiv.), the solution was stirred at room temperature under an inert atmosphere for 30 minutes. Benzoyl chloride (73.0 µL, 0.63 mmol, 1.1 equiv.) was added to the solution and the reaction was stirred 16 hours at room temperature under an inert atmosphere. The reaction was quenched by addition of ammonium chloride and extracted with ethyl acetate (3×30 mL). The combined organic extracts were dried (MgSO$_4$) and concentrated in vacuo. The crude material was purified by flash chromatography eluting with 10% ethyl acetate/hexane to afford 42 (71.0 mg) as a white solid (99% based on starting material recovery, 45% conversion); R$_f$ (20% ethyl acetate/petrol) 0.48; mp 66-68° C.; $^1$H NMR δ 8.46 (dt, J=8.4, 0.8 Hz, 1H; H-4), 8.04 (m, 2H; H-aromatic), 7.67 (app. dt, J=7.9, 1.0 Hz, 1H; H-aromatic), 7.57-7.39 (m, 4H; H-aromatic), 7.31 (ddd, J=8.0, 7.2, 0.9 Hz, 1H; H-5), 6.06 (ddt, J=17.2, 10.4, 5.8 Hz, 1H; H-17), 5.40 (dq, J=17.2, 1.5 Hz, 1H; H-18a), 5.28 (ddd, J=10.4, 2.6, 1.2 Hz, 1H; H-18b), 4.83 (dt, J=5.8, 1.3 Hz, 2H; H-16); $^{13}$C NMR δ 168.4 (C-8), 160.0 (C-3), 142.4 (C-aromatic), 134.7 (C-aromatic), 133.0 (C-aromatic), 132.5 (C-17), 131.9 (C-aromatic), 131.1 (C-aromatic), 130.5 (C-aromatic), 127.9 (C-aromatic), 124.6 (C-aromatic), 119.9 (C-aromatic), 119.1 (C-18), 116.5 (C-aromatic), 70.2 (C-16); LR MS (CI$^+$) m/z: 279 [M+H]$^+$; HR MS (CI$^+$) calcd for C$_{17}$H$_{15}$N$_2$O$_2$ [M+H]$^+$: 279.1134, found: 279.1131; IR (thin film, cm$^{-1}$) 3060 w, 2933 m, 2856 w, 1876 stg (C=O), 1548 stg (C=N), 1445 stg (C=N), 1406 stg, 1375 stg, 1336 stg (C=C), 1236 w, 1186 m, 878 stg, 750 stg (C=C), 694 m;

Synthesis of 43:

To a solution of 46 (100 mg, 0.58 mmol, 1.0 equiv.) in dry THF (10 mL) was added potassium t-butoxide (71 mg, 0.63 mmol, 1.1 equiv.), the solution was stirred at room temperature under an inert atmosphere for 30 minutes. Phenyl isocyanate (70 µL, 0.63 mmol, 1.1 equiv.) was added to the solution and the reaction was stirred 16 hours at room temperature under an inert atmosphere. The reaction was quenched by addition of ammonium chloride and extracted with ethyl acetate (3×30 mL). The combined organic extracts were dried (MgSO$_4$) and concentrated in vacuo. The crude material was purified by flash chromatography eluting with 20% ethyl acetate/hexane to afford 43 as a white solid (150 mg, 89%); R$_f$ (20% ethyl acetate/petrol) 0.44; mp 89-91° C.; $^1$H NMR δ 8.58 (br s, 1H; NH), 8.26 (d, J=8.5 Hz, 1H; H-7), 7.62-7.17 (m, 7H; H-aromatic), 7.04 (t, J=7.4 Hz, 1H; H-13), 6.09 (m, 1H; H-18), 5.44 (dq, J=17.2, 1.4 Hz, 1H; H-19a), 5.29 (dq, J=10.5, 1.4 Hz, 1H; H-19b), 4.89 (dt, J=5.7, 1.4 Hz, 2H; H-17); $^{13}$C NMR δ 157.8 (C-3), 149.0 (C-8), 140.6 (C7a), 137.3 (C-10), 132.2 (C-18), 130.2 (C-6), 129.1 (C-12), 124.0 (C-13), 122.9 (C-5), 119.9 (C-4), 119.6 (C-11), 118.8 (C-19), 116.6 (C-3a), 114.8 (C-7), 70.0 (C-17); LR MS (CI$^+$) m/z: 294 [M+H]$^+$; HR MS (CI$^+$) calcd for C$_{17}$H$_{16}$N$_3$O$_2$ [M+H]$^+$: 294.1243, found 294.1236; IR (thin film, cm$^{-1}$) 3375 m (N—H), 2928 w (C—H), 2852 w (C—H), 1716 stg (C=O), 1596 m (C=O), 1524 stg (C=N), 1446 m, 1406 m, 1361 m, 1344 m, 1219 m, 1097 m, 973 m, 928 m, 748 m;

Synthesis of 44:

To a solution of 46 (100 mg, 0.58 mmol, 1.0 equiv.) in dry THF (10 mL) was added triethylamine (90 µL, 0.64 mmol, 1.1 equiv.), the solution was stirred at room temperature under an inert atmosphere for 30 minutes. Benzyl sulfonyl chloride (121 mg, 0.64 mmol, 1.1 equiv.) was added to the solution and the reaction was stirred 16 hours at room temperature under an inert atmosphere. The reaction was quenched by addition of ammonium chloride and extracted with ethyl acetate (3×30 mL). The combined organic extracts were dried (MgSO$_4$) and concentrated in vacuo. The crude material was purified by flash chromatography eluting with 20% ethyl acetate/hexane to afford 44 as a white solid (68.0 mg, 37% conversion, 100% yield based on the recovered starting material); R$_f$ (20% ethyl acetate/petrol) 0.28; mp 100-101° C.; $^1$H NMR δ 8.06 (dt, J=8.4, 0.8 Hz, 1H; H-4), 7.78 (m, 2H; H-aromatic) 7.36 (m, 6H; H-aromatic), 5.99 (tdd, J=17.1, 10.5, 5.7 Hz, 1H; H-17), 5.35 (dq, J=17.2, 1.5 Hz, 1H; H-18a), 5.22 (dq, J=10.4, 1.2 Hz, 1H; H-18b), 4.85 (dt, J=5.7, 1.4 Hz, 2H; H-16); $^{13}$C NMR δ 161.2 (C-3), 143.1 (C-7a), 136.6 (C-9), 133.7 (C-12), 131.9 (C-14), 130.2 (C-6), 128.8 (C-11), 127.5 (C-10), 124.3 (C), 120.2 (C-4), 118.8 (C-15), 118.0 (C-3a), 114.2 (C), 70.2 (C-16); LR MS (CI$^+$) m/z: 315 [M+H]$^+$; HR MS (CI$^+$) calcd for C$_{16}$H$_{15}$N$_2$O$_3$S [M+H]$^+$: 315.0803, found: 315.0806; IR (thin film, cm$^{-1}$) 2920 m, 2847 m, 1543 m (C=N), 1372 stg (SO$_2$—N), 1342 m, 1181 stg (SO$_2$—N), 569 m.

Synthesis of 45:

To a solution of 46 (200 mg, 1.15 mmol, 1.0 equiv.) in dry THF (10.0 mL) was added potassium tert-butoxide (257 mg, 2.30 mmol, 2.0 equiv.). The solution was stirred for 1 hour at room temperature. To the resulting solution was added propylene oxide (400 µL, 5.70 mmol, 5.0 equiv.) and the reaction was stirred at room temperature for 16 hours. The reaction was quenched by addition of saturated ammonium chloride solution (20 mL) and extracted with ethyl acetate (3×50 mL). The combined organic extracts were dried (MgSO$_4$) and concentrated in vacuo. The crude material was purified by flash chromatography eluting with 20% ethyl acetate/hexane to give the desired product 45 as an orange oil (174 mg, 65%); R$_f$ (10% ethyl acetate/hexane) 0.08; $^1$H NMR δ 7.60 (dt, J=8.1, 1.0 Hz, 1H; H-4), 7.28 (ddd, J=8.4, 6.8, 1.0 Hz, 1H; H-6), 7.14 (dt, J=8.7, 1.0 Hz, 1H; H-7), 7.96 (ddd, J=7.9, 6.8, 0.8 Hz, 1H; H-5), 6.06 (ddt, J=17.2, 10.5, 5.6 Hz, 1H; H-13), 5.38 (dq, J=17.2, 1.6 Hz, 1H; H-14a), 5.22 (dq, J=10.5, 2.7 Hz, 1H; H-14b), 4.80 (dt, J=5.6, 1.4 Hz, 2H; H-12), 4.05 (m, 3H; H-8 and H-9), 1.15 (d, J=6.3 Hz, 3H; H-10); $^{13}$C NMR δ 155.7 (C-3), 142.0 (C-7a), 133.0 (C-13), 127.7 (C-6), 120.1 (C-4), 119.3 (C-5), 118.0 (C-14), 112.1 (C-3a), 108.5 (C-7), 69.7 (C-12), 67.5 (C-9), 54.4 (C-8), 20.1 (C-10); LR MS (CI⁺) m/z: 233 [M+H]⁺; HR MS (CI⁺) calcd for C₁₃H₁₇N₂O₂ [M+H]⁺: 233.1290; found 233.1282; IR (thin film, cm⁻¹) 3379 m (br)(O—H), 2971 stg, 2928 stg, 1617 stg, 1529 m (C=N), 1494 m (C=N), 1444 m, 1417 m.

Rearrangement Conditions:

To a solution of the substrate (allyloxyindazole specie) in dry THF was added palladium (0) triphenylphosphine tetrakis 5 mol. % The reaction was stirred at room temperature under an inert atmosphere for 16 hours and protected from the light with aluminium foil. The reaction was quenched by addition of ammonium chloride (10 mL) and extracted with ethyl acetate (3×30 mL). The combined organic extracts were dried (MgSO₄) and concentrated in vacuo. The crude material was purified by flash chromatography Rearrangement of 41:

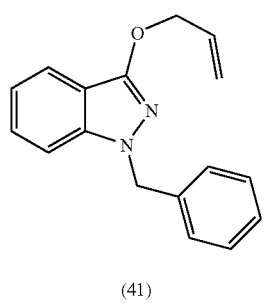

(41)

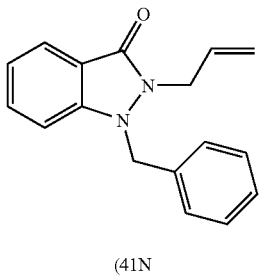

(41N)

41 (30.0 mg, 0.11 mmol) was submitted to the rearrangement conditions described above. After completion of the reaction, the reaction was quenched by addition of ammonium chloride (10 mL) and extracted with ethyl acetate (3×15 mL). The combined organic extracts were dried (MgSO₄) and concentrated in vacuo. The crude material was purified by flash chromatography eluting with 50% ethyl acetate/hexane to afford 41N as an orange oil (27.0 mg, 90%); R_f (50% ethyl acetate/petrol) 0.24; ¹H NMR δ 7.86 (dd, J=7.8, 1.1 Hz, 1H; H-aromatic), 7.50 (m, 1H; H-aromatic), 7.18 (m, 7H; H-aromatic), 5.82 (ddt, J=17.1, 10.1, 5.8 Hz, 1H; H-16), 5.21 (m, 2H, H-18), 4.84 (s, 2H; H-8), 4.52 (dt, J=5.7, 1.3 Hz, 2H; H-15); ¹³C NMR δ 163.2 (C-3), 149.2 (C-7a), 134.6, 132.4 (C-10 and C-11), 132.1 (C-6), 128.6 (C-aromatic), 128.1 (C-aromatic), 127.6 (C-aromatic), 124.1 (C-4), 121.9 (C-aromatic), 118.3 (C-aromatic), 117.9 (C-16), 111.6 (C-aromatic), 53.2 (C-8), 45.0 (C-15); LR MS (ES⁺) m/z: 287 [M+Na]⁺, HR MS (ES⁺) calcd for C₁₇H₁₆N₂ONa [M+Na]⁺: 287.1160, found: 287.1171; IR (thin film, cm⁻¹) 3060 m (C—H), 3026 m (C—H), 2924 m (C—H), 2856 w (C—H), 1661 stg (C=O), 1615 m (C=C), 1496 m, 1482 m, 1464 m, 1454 m, 1324 m, 1261 m, 1152 m, 990 m, 928 m, 753 m, 700 m.

Rearrangement of 44:

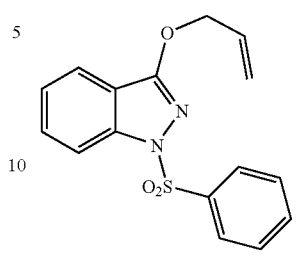

(44)

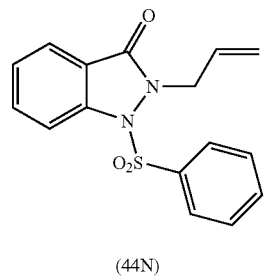

(44N)

44 (35.0 mg, 0.12 mmol) was submitted to the rearrangement conditions described above. After completion of the reaction, the reaction was quenched by addition of ammonium chloride and extracted with ethyl acetate (3×15 mL). The combined organic extracts were dried (MgSO₄) and concentrated in vacuo. The crude material was purified by flash chromatography eluting with 20% ethyl acetate/hexane to produce 44N as an orange oil (32.0 mg, 91%); R_f (50% ethyl acetate/petrol) 0.44; ¹H NMR δ 7.96 (dt, J=8.3, 0.8 Hz, 1H; H-aromatic), 7.60 (ddd, J=8.4, 7.3, 1.3 Hz, 1H; H-aromatic), 7.54 (ddd, J=7.8, 1.3, 0.8 Hz, 1H; H-aromatic), 7.41 (m, 3H; H-aromatic), 7.24 (m, 3H; H-aromatic), 5.77 (ddt, J=16.5, 10.1, 6.3 Hz, 1H; H-16), 5.26 (dq, J=17.1, 1.3 Hz, 1H; H-17a), 5.17 (ddd, J=10.1, 2.2, 1.0 Hz, 1H; H-17b), 4.75 (dt, J=6.3, 1.2 Hz, 2H; H-15); ¹³C NMR δ 166.5 (C-3), 145.6 (C-7a), 134.5 (C-aromatic), 133.5 (C-aromatic), 130.9 (C-16), 130.6 (C-aromatic), 128.8 (C-aromatic), 128.6 (C-aromatic), 126.8 (C-aromatic), 124.1 (C-aromatic), 121.8 (C-aromatic), 120.0 (C-17), 118.1 (C-aromatic), 49.9 (C-15); LR MS (EI⁺) m/z: 314 [M]⁺; HR MS (EI⁺) calcd for C₁₆H₁₄N₂O₃S [M]⁺: 314.0725, found: 314.0725; IR (thin film, cm⁻¹) 2928 m, 2853 m, 1704 stg (C=O), 1609 m, 1478 w, 1460 w, 1446 w, 1375 stg (SO₂N), 1182 stg (SO₂N), 1147 w, 1086 w, 761 stg (C=C), 729 m, 683 stg, 571 stg.

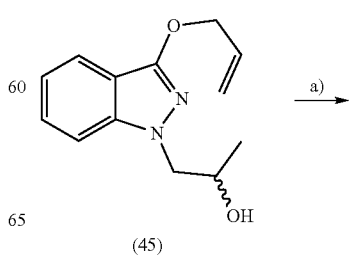

(45)

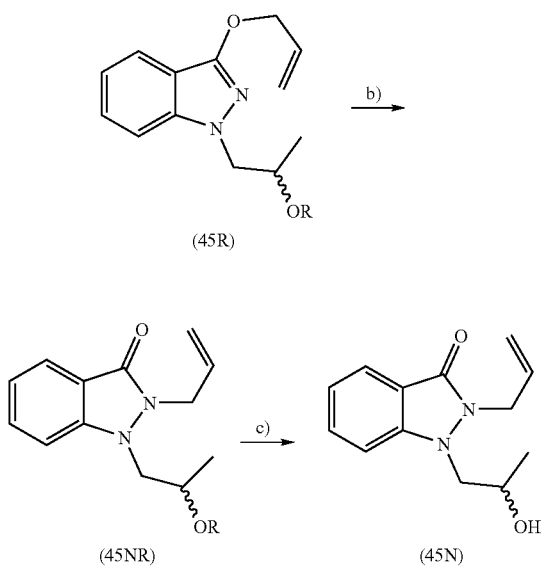

(45R)

(45NR)  (45N)

R = TIPS or Resin

Synthesis of 45R:

To a solution of 45 (80.0 mg, 0.34 mmol, 1.0 equiv.) in dry THF (5 mL) was added triethylamine (150 μL, 1.0 mmol, 3.0 equiv.). The solution was stirred 10 minutes at room temperature. To the resulting solution was added triisopropylsilyltriflate (180 μL, 0.52 mmol, 1.5 equiv.) and the reaction was stirred at room temperature for one hour. The reaction was then quenched by addition of saturated ammonium chloride solution (10 mL) and extracted with ethyl acetate (3×10 mL). The combined organic extracts were dried (MgSO$_4$) and concentrated in vacuo. The crude material was purified by flash chromatography eluting with 5% ethyl acetate/hexane to give the desired product 45TIPS as a colourless oil (114 mg, 85%); R$_f$ (10% ethyl acetate/hexane) 0.56; $^1$H NMR δ 7.56 (dt, J=8.1, 0.9 Hz, 1H; H-4), 7.22 (m, 2H; H-6 and H-7), 6.93 (ddd, J=7.84, 6.52, 1.15 Hz, 1H; H-5), 6.09 (ddt, J=17.2, 10.5, 5.6 Hz, 1H; H-16), 5.39 (dq, J=17.2, 1.59 Hz, 1H; H-17a), 5.22 (ddt, J=10.4, 2.80, 1.29 Hz, 1H; H-17b), 4.81 (dt, J=5.6, 1.39 Hz, 2H; H-15), 4.36 (sext., J=6.1 Hz, 1H; H-9), 4.04 (ABX, J=14.1, 6.2 Hz, 2H; H-8a and H-8b), 1.09 (d, J=6.09 Hz, 3H; H-10), 0.89 (s, 21H; H-13 and H-14); 13C NMR δ 155.3 (C-3), 142.0 (C-7a), 133.4 (C-16), 127.0 (C-6), 119.8 (C-4), 118.8 (C-5), 117.8 (C-17), 112.2 (C-3a), 109.0 (C-7), 69.6 (C-15), 68.0 (C-9), 56.0 (C-8), 22.0 (C-10), 17.9 (C-14), 12.4 (C-13); LR MS (CI$^+$) m/z: 389 [M+H]$^+$; HR MS (CI$^+$) calcd for C$_{22}$H$_{37}$N$_2$O$_2$Si [M+H]$^+$: 389.2624, found: 389.2627; IR (thin film, cm$^{-1}$) 2943 m, 2870 m, 2348 m, 1526 m (C=N), 988 m.

Synthesis of 45NR:

45TIPS (56.0 mg, 0.14 mmol) was submitted to the rearrangement conditions described above. After work up, the crude material was purified by flash chromatography eluting with 30% ethyl acetate/hexane to produce 45NTIPS as a colourless oil (34.0 mg, 60%); R$_f$ (20% ethyl acetate/hexane) 0.08, $^1$H NMR δ 7.77 (m, 1H; H-4), 7.42 (ddd, J=8.4, 7.1, 1.2 Hz, 1H; H-6), 7.11 (dt, J=8.4, 0.7 Hz, 1H; H-7), 7.03 (ddd, J=8.0, 7.1, 0.7 Hz, 1H; H-5), 5.72 (ddt, J=16.3, 10.6, 5.7 Hz, 1H; H-16), 5.10 (m, 2H; H-17), 4.53 (tt, J=5.6, 1.5 Hz, 2H; H-15), 4.08 (dd, J=12.4, 6.2 Hz, 1H; H-9), 3.68 (ABX system, J=15.4, 6.3 Hz, 2H; H-8), 0.97 (d, J=6.1 Hz, 3H; H-18), 0.92 (m, 21H; H-12, H-13 and H-14); $^{13}$C NMR δ 162.9 (C-3), 148.3 (C-7a), 132.5 (C-16), 132.0 (C-6), 124.1 (C-4), 121.0 (C-5), 117.8 (C-17), 116.8 (C-3a), 110.9 (C-7), 66.6 (C-9), 55.8 (C-8), 45.0 (C-15), 22.4, 18.0, 17.9, 12.5 (C-12, C-13, C-14, C-18); LR MS (CI$^+$) m/z: 389 [M+H]$^+$; HR MS (CI$^+$) calcd for C$_{22}$H$_{37}$N$_2$O$_3$Si [M+H]$^+$: 389.2624, found: 389.2629; IR (thin film, cm$^{-1}$) 2945 stg, 2866 stg, 1681 stg, 1621 m, 1484 m, 1464 m, 1263 w, 1144 m, 1112 w, 999 m, 920 w, 883 m, 750 m, 681 m.

Synthesis of 45N:

To a solution of 45NTIPS (30.0 mg, 0.077 mmol) in dry THF (2 mL) was added tetrabutyl ammonium fluoride (20 mg, 0.077 mmol, 1.0 equiv.) and the reaction was stirred at room temperature for 16 hours. The reaction was quenched by addition of ammonium chloride (10 mL) and extracted with ethyl acetate (3×15 mL). The combined organic extracts were dried (MgSO$_4$) and concentrated in vacuo. The crude material was purified by flash chromatography eluting with 50% ethyl acetate/hexane to afford 45N as a brown oil (11.0 mg, 60%); R$_f$ (100% ethyl acetate) 0.19; $^1$H NMR δ 7.77 (dt, J=0.9, 7.7 Hz, 1H; H-4), 7.46 (ddd, J=8.4, 7.1, 1.2 Hz, 1H; H-6), 7.14 (d, J=8.4 Hz, 1H; H-7), 7.07 (ddd, J=7.9, 7.2, 0.7 Hz, 1H; H-5), 5.73 (ddt, J=16.1, 10.6, 5.6 Hz, 1H; H-12), 5.11(m, 2H; H-13), 4.52 (dt, J=5.6, 1.5 Hz, 2H; H-11), 3.98 (m, 1H; H-9), 3.65 (ABX system, 2H; H-8), 1.12 (d, J=6.3 Hz, 3H; H-10); $^{13}$C NMR δ 163.0 (C-3), 148.9 (C-7a), 132.5 (C-12), 132.3 (C-6), 124.2 (C-4), 121.7 (C-5), 117.9 (C-13), 111.3 (C-7), 65.7 (C-9), 56.7 (C-8), 45.2 (C-11), 20.9 (C-10), C-3a missing, not visible by 2D experiment; HSQC and HMBC are in accordance with the proposed structure; LR MS (CI$^+$) m/z: 233 [M+H]$^+$; HR MS (CI$^+$) calcd for C$_{13}$H$_{17}$N$_2$O$_2$ [M+H]$^+$: 233.1290, found: 233.1299; IR (thin film, cm$^{-1}$) 3332 m (br)(0-H), 2971 w, 2924 w, 2860 stg, 1640 s (C=O), 1487 m, 1461 m, 1329 m, 1272 m, 1132 m, 940 m, 751 stg (C=C), 681 m, 543 m.

Figure 10:
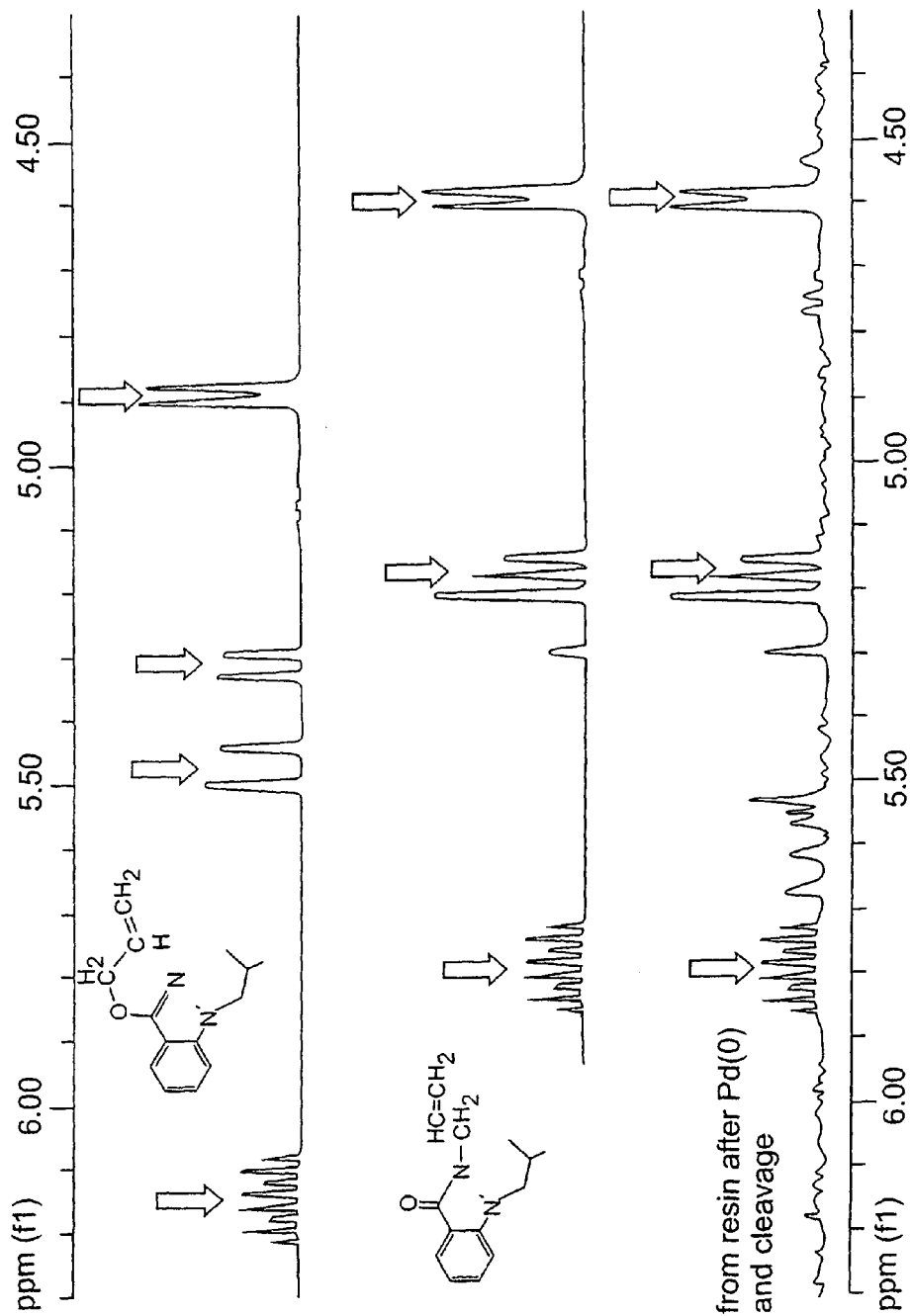
FIG. 10: Comparison of 45 (a), 45N (b) and the product made on solid phase (c) by $^1$H NMR.

Synthesis of 45N on Solid Support:

The same three-step synthesis was developed on the polyTIPS resin using the loading procedure as described previously, followed by the rearrangement induced by palladium (0). Finally, the products were cleaved from the resin according to the cleavage procedure described previously. The products obtained after cleavage (c) were compared by $^1$H NMR to the starting material 45 (a) and the final product 45N (b)(see FIG. 10).

Example 10

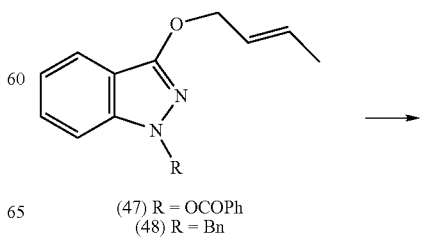

(47) R = OCOPh
(48) R = Bn

33

-continued

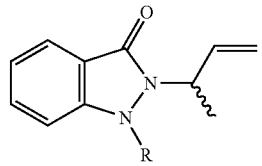

(49) R = OCOPh
(50) R = Bn

Synthesis of 49 by Palladium Catalysis:

To a solution of 47 (150 mg, 0.47 mmol) in dry THF (2 mL) was added 5 mol % of dichlorobis(acetonitrile) palladium (II)(6.00 mg, 0.023 mmol) under an inert atmosphere. The solution was stirred at room temperature for 16 hours under an inert atmosphere. The solvent was concentrated in vacuo and the reaction mixture was purified by flash chromatography eluting with 5% ethyl acetate/hexane to give 49 as an orange oil (146 mg, 97%); R$_f$ (20% ethyl acetate/petrol) 0.22; $^1$H NMR δ 7.73 (ddd, J=7.7, 1.7, 1.0 Hz, 2H; H-aromatic), 7.49 (ddd, J=8.6, 7.3, 1.3 Hz, 1H; H-aromatic), 7.34 (m, 5H; H-aromatic), 7.21 (m, 1H; H-aromatic), 6.12 (ddd, J=17.0, 10.3, 6.5 Hz, 1H; H-18), 5.30 (s, 2H; H-10), 5.09 (dq, J=15.0, 1.3 Hz, 1H; H-19a), 5.04 (dq, J=8.0, 1.3 Hz, 1H; H-19b), 4.83 (m, 1H; H-17), 1.53 (d, J=7.0 Hz, 3H; H-20); $^{13}$C NMR δ 166.3 (C-3), 151.9 (C-7a), 144.1 (C-aromatic), 136.8 (C-18), 134.2 (C-aromatic), 133.4 (C-aromatic), 129.0 (C-aromatic), 128.8 (C-aromatic), 124.8 (C-aromatic), 123.6 (C-aromatic), 119.8 (C-aromatic), 116.5 (C-19), 115.6 (C-aromatic), 69.6 (C-10), 59.3 (C-17), 17.5 (C-20); LR MS (CI$^+$) m/z: 323.14 [M+H]$^+$; HR MS (CI$^+$) calcd for C$_{19}$H$_{19}$N$_2$O$_3$ [M+H]$^+$: 323.1396, found: 323.1398; IR (thin film, cm$^{-1}$) 3069 m, 3030 m, 2979 m, 2937 m, 1742 stg (C=O), 1700 stg (C=O), 1614 stg (C=C), 1462 m.

Synthesis of 50 by Microwave Irradiations:

A solution of 48 (15.0 mg, 0.054 mmol) in dry DMF (1 mL) was submitted to microwave irradiation (200° C., 300 W) for 10 min under a maximum pressure of 96 psi. The crude reaction was cooled down at room temperature. Water (10 mL) was added to the mixture and the aqueous solution was extracted with ether (2×5 mL). The combined organic extracts were washed with water (5 mL) and dried (MgSO$_4$). The crude material was purified by flash chromatography eluting with 30% ethyl acetate/hexane to afford 50 as a orange oil (10.0 mg, 67%). R$_f$ (20% ethyl acetate/petrol) 0.07; $^1$H NMR δ 7.76 (dt, J=7.8 Hz, 1H; H-aromatic), 7.36 (ddd, J=8.4, 7.2, 1.2 Hz, 1H; H-aromatic), 7.12 (m, 5H; H-aromatic), 7.05 (m, 4H; H-aromatic), 6.89 (d, J=8.3.0 Hz, 1H; H-aromatic), 6.10 (ddd, J=17.5, 10.6, 5.0 Hz, 1H; H-16), 5.18 (ddd, J=12.6, 1.9, 0.9 Hz, 1H; H-17a), 5.13 (ddd, J=5.7, 1.9, 0.9 Hz, 1H; H-17b), 5.00 (m, 1H; H-15), 4.77 (ABX system, 2H; H-8), 1.46 (d, J=7.0 Hz, 3H; H-18); $^{13}$C NMR δ 160.4 (C-3), 150.7 (C-7a), 138.0 (C-16), 132.3 (C-aromatic), 130.9 (C-aromatic), 128.7 (C-aromatic), 128.0 (C-aromatic), 127.6 (C-aromatic), 124.2 (C-aromatic), 122.1 (C-aromatic), 116.1 (C-17), 112.0 (C-aromatic), 55.0 (C-8), 53.5 (C-15), 17.3 (C-18), C-3a missing on spectrum; LR MS (ES$^+$) m/z: 301 [M+Na]$^+$; HR MS (ES$^+$) calcd for C$_{18}$H$_{18}$N$_2$ONa [M+Na]$^+$: 301.1317, found: 301.1319 ; IR (thin film, cm$^{-1}$) 2920 stg, 2852 stg, 1725 w, 1674 stg (C=O), 1615 m, 1483 w, 1457 m, 1262 m, 1075 w, 1019 w, 798 m, 751 m (C=C), 700 m.

Example 11

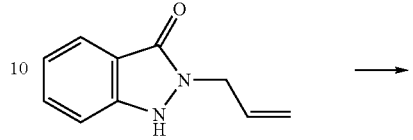

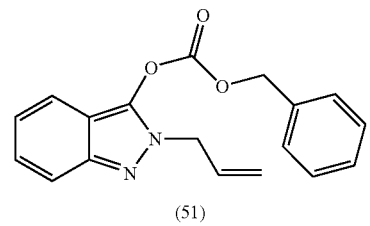

Synthesis of 51

To a solution of N2-allyl indazolinone (250 mg, 1.44 mmol, 1.0 equiv.) in dry THF (15 mL) was added triethylamine (241 µL, 1.73 mmol, 1.20 equiv.) and the solution was stirred at room temperature under an inert atmosphere for 30 minutes. Benzyl chloroformate (225 µL, 1.58 mmol, 1.10 equiv.) was added and the solution was stirred under the same conditions for 1 hour. The reaction was quenched by addition of saturated ammonium chloride solution (20 mL) and extracted with ethyl acetate (3×30 mL). The combined organic extracts were dried (MgSO$_4$) and concentrated in vacuo. The crude material was purified by flash chromatography eluting with 20% ethyl acetate/hexane to afford 51 as an orange oil (431 mg, 97%); R$_f$ (20% ethyl acetate/petrol) 0.15; $^1$H NMR δ 7.61 (d, J=8.8 Hz, 1H; H-7), 7.44 (m, 6H; H-aromatic), 7.25 (m, 1H; H-6), 7.05 (m, 1H; H-5), 5.98 (m, 1H; H—), 5.33 (s, 2H; H-14), 5.18 (d, J=5.9Hz, 1H; H-10), 5.13 (d, J=12.7 Hz, 1H; H-10), 4.89 (d, J=5.9 Hz, 2H; H-8); $^{13}$C NMR δ 151.2 (C-12), 147.1 (C-7a), 136.8 (C-3), 133.9 (C-15), 131.3 (C-9), 129.3 (C-aromatic), 128.8 (C-aromatic), 126.6 (C-6), 121.9 (C-5), 118.9 (C-10), 118.6 (C-4), 117.8 (C-7), 110.4 (C-3a), 71.8 (C-14), 52.0 (C-8); HSQC and HMBC are consistent with the proposed structure; LR MS (EI$^+$) m/z: 308 [M]$^+$; HR MS (EI$^+$) calcd for C$_{18}$H$_{16}$N$_2$O$_3$ [M]$^+$: 308.1161, found: 308.1157; IR (thin film, cm$^{-1}$) 3037 w, 2925 w, 1750 stg (C=O), 1700 stg, 1615 w, 1457 stg, 1389 m, 1280 stg, 752 stg.

The invention claimed is:

1. A method for converting at least one compound having the structure B:

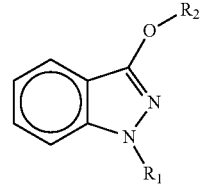

B to a compound having the structure A:

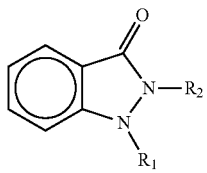

comprising exposing the at least one compound of structure B to microwave energy to convert said compound into a compound of structure A;
wherein $R_1$ is selected from the group consisting of alkyl, aminoalkyl, acylamino, acyloxy, alkoxycarbonyl, alkoxy, alkylaryl, hydroxyalkyl, thioalkyl, acyl, amino, hydroxy, thio, aryloxy, arylalkoxy, hydrogen, alkynyl, halogen, cyano, sulfhydryl, carbamoyl, nitro, trifluoromethyl, and heterocyclyl; and
$R_2$ has the following structure:

—C($R_{13}$)($R_{14}$)—C($R_{15}$)=C($R_{16}$)($R_{17}$)

wherein each group $R_{13}$, $R_{14}$, $R_{15}$, $R_{16}$, and $R_{17}$ is independently selected from the group consisting of hydrogen, —CH$_3$, —C$_2$H$_5$, and an aryl group.

2. The method of claim 1 wherein $R_2$ has the structure:

—C($R_{13}$)($R_{14}$)—C($R_{15}$)=C($R_{16}$)($R_{17}$)

wherein each of $R_{13}$, $R_{14}$, $R_{15}$ and $R_{16}$ is independently selected from the group consisting of hydrogen, —CH$_3$, and —C$_2$H$_5$; and $R_{17}$ is an aryl group.

3. The method of claim 1 wherein $R_{13}$ to $R_{16}$ are each hydrogen and $R_{17}$ is an aryl group.

4. The method of claim 1 wherein $R_{17}$ is phenyl.

5. The method of claim 1 wherein $R_1$ is a heterocyclyl which is substituted with one or more substituents selected from the group consisting of alkyl, halo, hydroxy, amino, thio, lower alkoxy, lower alkylthio, lower alkylamino, nitro, phenoxy, benzyloxy, and hydrogen.

6. The method of claim 1 wherein the step of exposing the compound of structure B to microwave energy is conducted at a temperature of 150° C. or higher.

7. The method of claim 1 wherein the step of exposing the compound of structure B to microwave energy is conducted at a pressure of 15psi or higher.

8. The method of claim 1 wherein an isomeric mixture of compounds of structure B is exposed to microwave energy and converted into compounds of structure A.

* * * * *